US012778491B2

(12) United States Patent
Salese et al.

(10) Patent No.: US 12,778,491 B2
(45) Date of Patent: Nov. 3, 2026

(54) SYSTEMS, DEVICE, AND METHODS FOR CURLY HAIR ASSESSMENT AND PERSONALIZATION

(71) Applicant: L'OREAL, Paris (FR)

(72) Inventors: Michelle Salese, South Plainfield, NJ (US); Ronak Rughani, Edison, NJ (US)

(73) Assignee: L'Oreal, Paris (FR)

( * ) Notice: Subject to any disclaimer, the term of this patent is extended or adjusted under 35 U.S.C. 154(b) by 320 days.

(21) Appl. No.: 18/375,225

(22) Filed: Sep. 29, 2023

(65) Prior Publication Data

US 2024/0108280 A1 Apr. 4, 2024

Related U.S. Application Data

(60) Provisional application No. 63/412,045, filed on Sep. 30, 2022.

(30) Foreign Application Priority Data

Jan. 19, 2023 (FR) ...................................... 2300498

(51) Int. Cl.

| | |
|---|---|
| ***A61B 5/00*** | (2006.01) |
| ***G16H 10/60*** | (2018.01) |
| ***G16H 20/00*** | (2018.01) |
| ***G16H 30/40*** | (2018.01) |

(52) U.S. Cl.

CPC ............. *A61B 5/448* (2013.01); *G16H 10/60* (2018.01); *G16H 20/00* (2018.01); *G16H 30/40* (2018.01)

(58) Field of Classification Search

CPC ..................................................... A61B 5/448

See application file for complete search history.

(56) References Cited

U.S. PATENT DOCUMENTS

| | | | | |
|---|---|---|---|---|
| 2006/0265244 A1* | 11/2006 | Baumann | ............... | A61B 5/441 424/59 |
| 2012/0116187 A1* | 5/2012 | Hayes | .................. | A61B 5/7264 600/587 |
| 2014/0351078 A1* | 11/2014 | Kaplan | .............. | G06Q 30/0631 705/26.7 |
| 2018/0342055 A1 | 11/2018 | Lyman et al. | | |

(Continued)

OTHER PUBLICATIONS

Written Opinion and Search Report issued Aug. 23, 2023 in French Patent Application No. 2300498.

(Continued)

*Primary Examiner* — Michael T. Holtzclaw

(74) *Attorney, Agent, or Firm* — Christensen O'Connor Johnson Kindness PLLC

(57) ABSTRACT

A system is provided that includes at least one server device; and a mobile user device that includes processing circuitry configured to execute an application that receives an input of user information regarding a plurality of characteristics of at least the hair of a user including at least a curl pattern of the user; and receives an input of a desired result of treatment of the hair of the user. The processing circuitry of the at least one server device receives the input of user information and the input of the desired result of treatment and outputs a product or treatment recommendation based at least partially on the determined curl pattern of the user and the desired result of the user.

15 Claims, 34 Drawing Sheets

(56) References Cited

U.S. PATENT DOCUMENTS

| | | | | |
|---|---|---|---|---|
| 2018/0349979 | A1* | 12/2018 | Robinson | G06F 16/583 |
| 2019/0102894 | A1 | 4/2019 | Deulin et al. | |
| 2019/0350514 | A1 | 11/2019 | Purwar et al. | |
| 2019/0355115 | A1 | 11/2019 | Niebauer et al. | |
| 2020/0226660 | A1* | 7/2020 | Wunderle | G06V 10/82 |
| 2021/0312150 | A1 | 10/2021 | Nater et al. | |
| 2021/0406589 | A1 | 12/2021 | Yadav et al. | |
| 2021/0406996 | A1 | 12/2021 | Yu et al. | |
| 2022/0164852 | A1* | 5/2022 | Punyani | G06V 10/82 |
| 2022/0366607 | A1 | 11/2022 | Bojan et al. | |
| 2023/0315780 | A1 | 10/2023 | Fawaz et al. | |
| 2024/0029345 | A1 | 1/2024 | Selvert et al. | |

OTHER PUBLICATIONS

Gunasegaran, T., and Y-N Cheah, "Evolutionary Cross Validation," 2017 8th International Conference on Information Technology (ICIT), Amman, Jordan, 2017, pp. 89-95.

Written Opinion and Search Report issued Aug. 22, 2023 in French Patent Application No. 2300497, filed Jan. 19, 2023, 7 pages.

Written Opinion and Search Report issued Aug. 23, 2023 in French Patent Application No. 2300500, filed Jan. 19, 2023, 8 pages.

Non-Final Office Action mailed Oct. 8, 2025, issued in U.S. Appl. No. 18/375,262, filed Sep. 29, 2023, 17 pages.

Non-Final Office Action mailed Sep. 11, 2025, issued in U.S. Appl. No. 18/375,163, filed Sep. 29, 2023, 21 pages.

* cited by examiner

PERSONAL INFORMATION

CURRENT HAIR JOURNEY

DESIRED BENEFITS

| Curl Type | Other Characteristics<br>Porosity, elasticity, coloring, chemical treatment, heat styling | Pain Points | Recommendations |
|---|---|---|---|
| Texture Type 2 Waves also known as 2A-2B. Varies from Loose "S" pattern to a defined "S" pattern. The best way to picture this is as beachy waves. | • **TEXTURE**: Thin to thick or combination.<br>• **GROWTH PATTERN**: Don't start at the roots.<br>• **BODY / VOLUME:** Some body, volume or end-wave curve movement.<br>• **ELASTICITY:** Marginal stretching with return.<br>• **POROSITY:** Compact to slightly raised cuticle. | Can be prone to flyaway and frizz.<br>Not Straight Enough, Not Wavy Enough<br>Easily Weighed Down<br>Flat Roots<br>Can be Damaged<br>More prone to oily roots | May require products like mousse or gel stylers to give it a more defined wavy texture.<br>Use a lightweight serum to smooth Out Hair<br>Use root volumizing products<br>Detangle hair frequently<br>Look for products with Fatty alcohols, like cetyl, lauryl, and stearyl. |
| Texture Type 3 Wavy/Curly also known as 2C-3A. Often characterized as wide waves to loose curls. If your Texture tends to,grow down from the scalp in alternating C-Shape wave patterns keep your strands in this category. | •**TEXTURE:** Can have a combination texture. Hair has wider waves or/and thick and full with much body.<br>•**GROWTH PATTERN:** The curls usually do not start at the roots of the hair but often get tighter near the ends<br>•**BODY / VOLUME:** Some body, volume or end wave movement<br>•**ELASTICITY:** Stretching with moderate return<br>•**POROSITY:** Slightly raised to raised cuticle. Good to moderate absorption. | Lots of body and movement<br>Frizzez easily<br>Can be more difficult to detangle<br>Can be Damaged<br>Prone to dryness | Use a Leave-In Treatment<br>Use a sulfate free shampoo<br>Clarify hair once in a while<br>Use a styling cream, cream gel, or styling milk for less frizz but more definition.<br>Oils, butters and silicone can help with definition |
| Texture Type 4 Curly also known as 3B. Often characterized as tight curls, mixed curl patterns of loop to spirals to ringlets. If your Texture tends to, grow down from the scalp in these mixed curl patterns then keep your strands in this category. | •**TEXTURE:** Mixed curl patterns. Loops to spirals, ringlets<br>•**GROWTH PATTERN:** Grows down from scalp in mixed pattern curls<br>• **BODY / VOLUME:** Natural bounce, easy to create volume.<br>• **ELASTICITY:** Stretching with moderate spring-back.<br>• **POROSITY:** Slightly raised to raised cuticle. Moderate absoprtion. | Likely to frizz.<br>Prone to dryness.<br>Tangles easily.<br>Has lots of volume.<br>Can have product build up. | Nourish With a Deep Conditioner<br>Use a Leave-In Treatment<br>Use a sulfate free shampoo<br>Clarify hair once in a while<br>Use a styling cream, cream gel, or styling milk for less frizz but more definition.<br>Oils, butters and silicone can help with definition |
| Texture Type 5 Very Curly also known as 3C. Curls are tight, but not necessarily all the same diameter. You may find you have a blend of a few different textures. If your Texture tends to,grow down from the scalp then curls in defined S-shapes keep your strands in this category. | • **TEXTURE**. Defined curl with s-shapes forming into coils.<br>• **GROWTH PATTERN**: Grows down from scalp, then curls in defined S-shapes.<br>• **BODY / VOLUME:** Some movement. Prone to compactness.<br>• **ELASTICITY:** Stretching with immediate spring-back<br>• **POROSITY:** Raised cuticle. Moderate to resistant absorption. | Likely to frizz and tangle<br>Can be damaged<br>Prone to Dryness<br>Requires extra moisture and lots of care because of its fragile nature | Nourish With a Deep Conditioner<br>Use a Leave-In Treatment<br>Use a sulfate free shampoo<br>Clarify hair once in a while<br>Oils, butters and silicone can help with definition<br>Treatment mask is great for extremely dry 3C hair<br>Usestyling butters and oils |

FIG. 18B

| Curl Type | Other Characteristics<br>Porosity, elasticity, coloring, chemical treatment, heat styling | Pain Points | Recommendations |
|---|---|---|---|
| Texture Type 6 Coiled also known as 4A. Springy coils with definition. The hair can have a very tight "S" pattern or a slightly looser "Z". It could also be a mix of both. If your Texture tends to, have distinct, medium coils that are close to your scalp keep your strands in this category. | • **TEXTURE:** Medium Coils are Close to the Scalp. Loose Afro<br>• **GROWTH PATTERN:** Grows up and away from the scalp, then curls.<br>• **BODY / VOLUME:** Some volume. Likely to be compact with less movement.<br>• **ELASTICITY:** Moderate shrinkage. Stretching with moderate spring back.<br>• **POROSITY:** Raised cuticle. Resistant to aborption. | Prone to dryness<br>Prone to shrinkage<br>Fragile<br>Prone to damage<br>Can lack definition without manual manipulation<br>Can get unruly when touched or brushed too often.<br>Build Up | Use a Leave-In Treatment<br>Use a sulfate free shampoo<br>Clarify hair once in a while<br>Oils, butters and silicone can help with definition<br>Usestyling butters and oils<br>Deep Condition Weekly |
| Texture Type 7 Very Coiled also known as 4B. Hair bends in more of a "Z" than "S" shape and the strands are closer together, creating plenty of volume. If your Texture tends to, have distinct, spring coils closer to the scalp this keep your curl type into this category | • TEXTURE: Tight Afro<br>• GROWTH PATTERN: Coils directly from scalp but tight at base<br>• BODY / VOLUME: Minimal Volume. Some compaction, no movement.<br>• ELASTICITY: Stretching with immediate spring back.<br>• POROSITY: Raised cuticle. Highly resistant to absorpotion. | Shows no definite pattern<br>Prone to dryness<br>Prone to shrinkage<br>Fragile<br>Prone to damage<br>Build up | Use a Leave-In Treatment<br>Use a sulfate free shampoo<br>Treatment mask weekly<br>Usestyling butters and oils<br>Deep Condition Weekly<br>Use Cleansing conditoners<br>Treat with products that have oils, Polyquats & glycerin |
| Texture Type 8 Zig Zag Coiled also known as 4C coils are even more tightly packed, which means the exact "Z" shape is not always visible. If your Texture tends to grow directly from the scalp in the zig-zag patterns it will fall in this category. | • **TEXTURE:** Extremely tight Afro- Interlocking coils and zig-zag patterns..<br>• **GROWTH PATTERN:**Coils directly from scalp but tight at base.<br>• **BODY / VOLUME:** More Volume than body.t<br>• **ELASTICITY:** Stretching with immediate spring back.<br>• **POROSITY:** Raised cuticle.Super resistant to absorption. | Shows no definite pattern<br>Prone to dryness<br>Prone to shrinkage<br>Fragile<br>Prone to damage<br>Build UP | Use a Leave-In Treatment<br>Use a sulfate free shampoo<br>Clarify hair once in a while<br>Treatment mask weekly<br>Deep Condition Weekly<br>Use Cleansing conditoners<br>Treat with products that have oils, Polyquats & glycerin |

FIG. 18C

SYSTEMS, DEVICE, AND METHODS FOR CURLY HAIR ASSESSMENT AND PERSONALIZATION

CROSS-REFERENCE TO RELATED APPLICATIONS

This application claims the benefit of priority to non-provisional application No. 63/412,045 filed on Sep. 30, 2022, and French application Serial No. 2300498 filed on Jan. 19, 2023, the entire contents of which are incorporated herein by reference.

BACKGROUND

Field

The disclosure herein generally relates to a system, apparatus, and method for diagnosing a type of curly hair of a user, providing a recommendation on a product or treatment for the user, and utilizing user and social feedback to enhance both the curl diagnosis and the product recommendation.

SUMMARY

In an embodiment, a system is provided comprising: at least one server device; and a mobile user device that includes processing circuitry configured to execute an application that receives an input of user information regarding a plurality of characteristics of at least the hair of a user including at least a curl pattern of the user; and receives an input of a desired result of treatment of the hair of the user, wherein the processing circuitry of the at least one server device receives the input of user information and the input of the desired result of treatment and outputs a product or treatment recommendation based at least partially on the determined curl pattern of the user and the desired result of the user.

In an embodiment, the user inputs a desired result by providing textual descriptors of a desired condition of the hair of the user.

In an embodiment, the user inputs a desired result based on selecting an image of a type of curl pattern.

In an embodiment, the processing circuitry of the at least one server device determines the product or treatment recommendation by inputting the input of user information and the input of the desired result of treatment into a neural network that is trained to output recommendations based on a combination of image information and textual information.

In an embodiment, the processing circuitry of the at least one server device determines the product or treatment recommendation by inputting the input of user information and the input of the desired result of treatment into a look-up table.

In an embodiment, the outputted product or treatment recommendation includes a recommendation of products and/or treatment related to at least one of hair care, styling care, and scalp care.

In an embodiment, the outputted product or treatment recommendation includes guides related to the science of hair, which explains hair structure and hair growth using at least one of illustrations, publications, video, and/or animation.

In an embodiment, after outputting the product or treatment recommendation to the user, the processing circuitry of the mobile user device receives an image of a plurality of hair care products that are at a retail location where the user is located, and the processing circuitry of the at least one server device is configured to generate a recommendation of at least one of the hair care products that are at the retail location.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein:

FIGS. 18A, 18B, and 18C show examples of look-up tables.

FIG. 30B shows that if the user selects an option, then a new screen is displayed.

DETAILED DESCRIPTION OF THE EMBODIMENTS

In hair care and maintenance, there are many types of curly hair and consumers with curly hair want the best and most appropriate care for their individual curl and hair type, shape, and form. There are many of different curl pattern charts showing types of curl patterns, and a times it can be difficult to self-diagnose the state, type, and needed care for your hair. Choosing the wrong pattern, may lead to selection the wrong product, which can result in the wrong outcome or a less than optimal result. Therefore, what is need is an application that can provide a method of diagnosing a consumer's curly hair and providing a recommendation on a product or treatment to provide a desired result to the consumer.

The below embodiments describe a system, a device, or an application ("App") that can receive as at least one input a user's curly hair pattern based on a picture of user's hair, and diagnose a curl pattern, how shiny the hair is, color and texture. Based on this diagnosis the application will advise a specific product or regimen of products from a designated brand and the ability to purchase on the spot.

There is also an opportunity for the ability to adapt the diagnosis and recommendations on the evolution of the consumers' hair and needs. One month a consumer can receive a diagnosis based on their hair being dry and perhaps the consumers hair evolves and their hair is now oily. With this new information they can count on the application to redirect the diagnosis and recommendation based on the adaptation of their hair.

[System]

Figure 1:
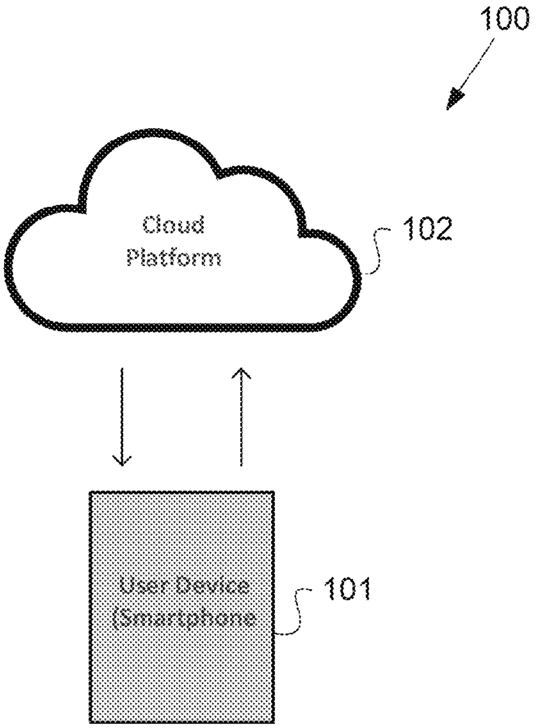
FIG. 1 shows an overall system 100 according to an embodiment.

FIG. 1 shows an overall system 100 according to an embodiment. The basic required components are a user device 101 (such as a smartphone) and one or more server devices 102 (such as a cloud platform). A hardware description of these components will be provided later. The smartphone is shown to include a smartphone application ("app") Usage of the smartphone application itself involves the user actually providing inputs making selections that lead to the functionality of the curl diagnosis and the product recommendations.

The smartphone application also performs interactive communication with the cloud platform. For instance, the smartphone application can receive the selection of relevant looks are described above, and it can also provide direct user feedback from the user on the looks the cloud platform previously sent and it can notify the cloud platform on the colors and recipes actually selected by the user and dispensed by the dispenser. Such feedback can provide a form of machine learning to the cloud platform and improve the algorithms used by the cloud platform.

Figure 2:
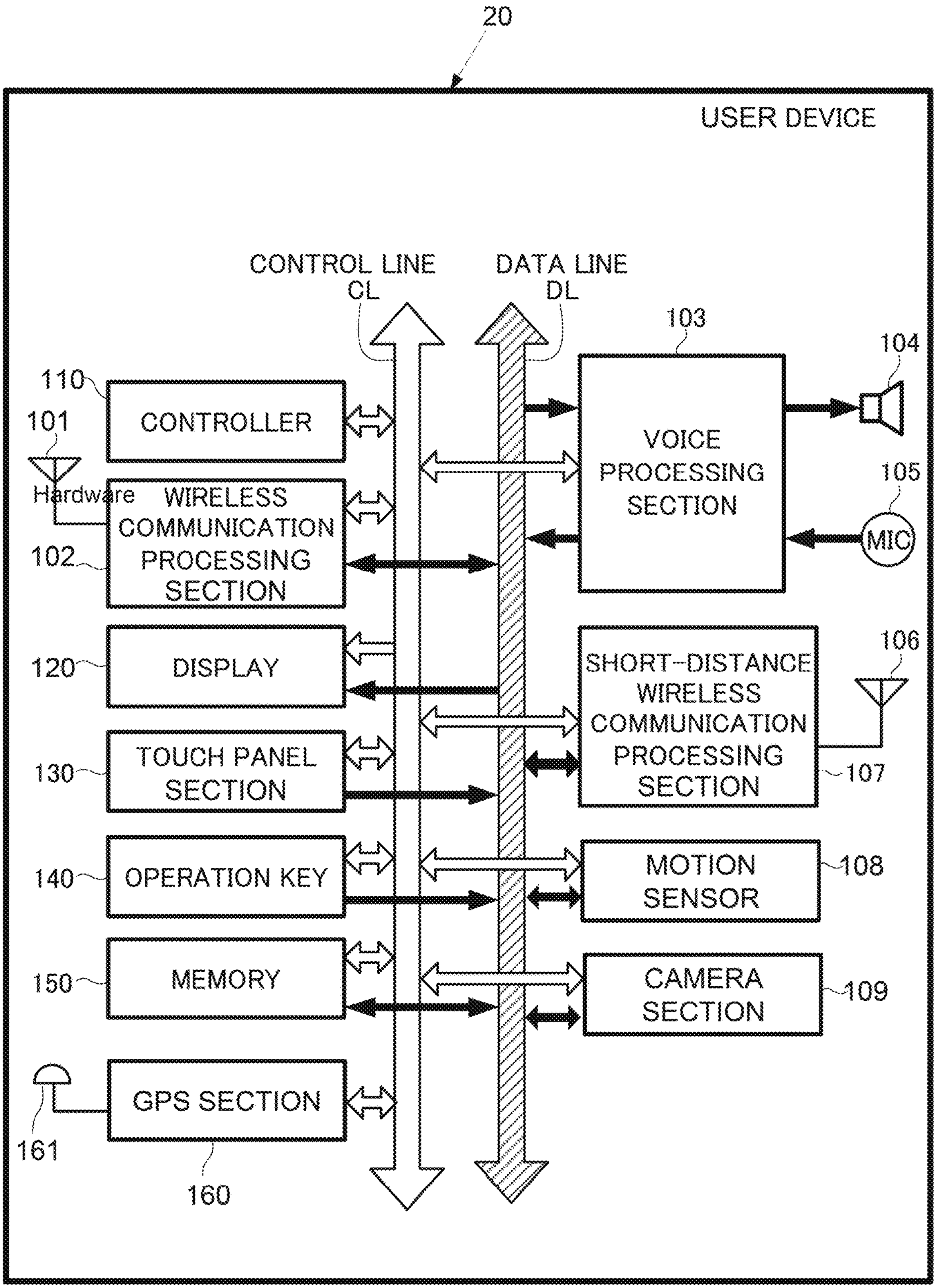
FIG. 2 is a more detailed block diagram illustrating an exemplary user device 20 according to certain embodiments.

FIG. 2 is a more detailed block diagram illustrating an exemplary user device 20 according to certain embodiments of the present disclosure. In certain embodiments, user device 20 may be a smartphone. However, the skilled artisan will appreciate that the features described herein may be adapted to be implemented on other devices (e.g., a laptop, a tablet, a server, an e-reader, a camera, a navigation device, etc.). The exemplary user device 20 of FIG. 9 includes a controller 110 and a wireless communication processor 102 connected to an antenna 101. A speaker 104 and a microphone 105 are connected to a voice processor 103.

The controller 110 is an example of the control unit 21 shown in FIG. 1 and may include one or more Central Processing Units (CPUs), and may control each element in the user device 20 to perform functions related to communication control, audio signal processing, control for the audio signal processing, still and moving image processing and control, and other kinds of signal processing. The controller 110 may perform these functions by executing instructions stored in a memory 150. Alternatively or in addition to the local storage of the memory 150, the functions may be executed using instructions stored on an external device accessed on a network or on a non-transitory computer readable medium. As described above in relation to FIG. 1, the controller 110 may execute instructions allowing the controller 110 to function as the display control unit 211, operation management unit 212 and game management unit 213 depicted in FIG. 1.

The memory 150 is an example of the storage unit 22 shown in FIG. 1 and includes but is not limited to Read Only Memory (ROM), Random Access Memory (RAM), or a memory array including a combination of volatile and non-volatile memory units. The memory 150 may be utilized as working memory by the controller 110 while executing the processes and algorithms of the present disclosure. Additionally, the memory 150 may be used for long-term storage, e.g., of image data and information related thereto.

The user device 20 includes a control line CL and data line DL as internal communication bus lines. Control data to/from the controller 110 may be transmitted through the control line CL. The data line DL may be used for transmission of voice data, display data, etc.

The antenna 101 transmits/receives electromagnetic wave signals between base stations for performing radio-based communication, such as the various forms of cellular telephone communication. The wireless communication processor 102 controls the communication performed between the user device 20 and other external devices via the antenna 101. For example, the wireless communication processor 102 may control communication between base stations for cellular phone communication.

The speaker 104 emits an audio signal corresponding to audio data supplied from the voice processor 103. The microphone 105 detects surrounding audio and converts the detected audio into an audio signal. The audio signal may then be output to the voice processor 103 for further processing. The voice processor 103 demodulates and/or decodes the audio data read from the memory 150 or audio data received by the wireless communication processor 102 and/or a short-distance wireless communication processor 107. Additionally, the voice processor 103 may decode audio signals obtained by the microphone 105.

The exemplary user device 20 may also include a display 120, a touch panel 130, an operation key 140, and a short-distance communication processor 107 connected to an antenna 106. The display 120 may be a Liquid Crystal Display (LCD), an organic electroluminescence display panel, or another display screen technology. In addition to displaying still and moving image data, the display 120 may display operational inputs, such as numbers or icons which may be used for control of the user device 20. The display 120 may additionally display a GUI for a user to control aspects of the user device 20 and/or other devices. Further, the display 120 may display characters and images received by the user device 20 and/or stored in the memory 150 or accessed from an external device on a network. For example, the user device 20 may access a network such as the Internet and display text and/or images transmitted from a Web server.

The touch panel 130 may include a physical touch panel display screen and a touch panel driver. The touch panel 130 may include one or more touch sensors for detecting an input operation on an operation surface of the touch panel display screen. The touch panel 130 also detects a touch shape and a touch area. Used herein, the phrase "touch operation" refers to an input operation performed by touching an operation surface of the touch panel display with an instruction object, such as a finger, thumb, or stylus-type instrument. In the case where a stylus or the like is used in a touch operation, the stylus may include a conductive material at least at the tip of the stylus such that the sensors included in the touch panel 130 may detect when the stylus approaches/contacts the operation surface of the touch panel display (similar to the case in which a finger is used for the touch operation).

One or more of the display 120 and the touch panel 130 are examples of the touch panel display 25 depicted in FIG. 1 and described above.

In certain aspects of the present disclosure, the touch panel 130 may be disposed adjacent to the display 120 (e.g., laminated) or may be formed integrally with the display 120. For simplicity, the present disclosure assumes the touch panel 130 is formed integrally with the display 120 and therefore, examples discussed herein may describe touch operations being performed on the surface of the display 120 rather than the touch panel 130. However, the skilled artisan will appreciate that this is not limiting.

For simplicity, the present disclosure assumes the touch panel 130 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 130 may include transparent electrode touch sensors arranged in the X-Y direction on the surface of transparent sensor glass.

The touch panel driver may be included in the touch panel 130 for control processing related to the touch panel 130, such as scanning control. For example, the touch panel driver may scan each sensor in an electrostatic capacitance transparent electrode pattern in the X-direction and Y-direction and detect the electrostatic capacitance value of each sensor to determine when a touch operation is performed. The touch panel driver may output a coordinate and corresponding electrostatic capacitance value for each sensor. The touch panel driver may also output a sensor identifier that may be mapped to a coordinate on the touch panel display screen. Additionally, the touch panel driver and touch panel sensors may detect when an instruction object, such as a finger is within a predetermined distance from an operation surface of the touch panel display screen. That is, the instruction object does not necessarily need to directly contact the operation surface of the touch panel display screen for touch sensors to detect the instruction object and perform processing described herein. For example, in certain embodiments, the touch panel 130 may detect a position of a user's finger around an edge of the display panel 120 (e.g., gripping a protective case that surrounds the display/touch panel). Signals may be transmitted by the touch panel driver, e.g. in response to a detection of a touch operation, in response to a query from another element based on timed data exchange, etc.

The touch panel 130 and the display 120 may be surrounded by a protective casing, which may also enclose the other elements included in the user device 20. In certain embodiments, a position of the user's fingers on the protective casing (but not directly on the surface of the display 120) may be detected by the touch panel 130 sensors. Accordingly, the controller 110 may perform display control processing described herein based on the detected position of the user's fingers gripping the casing. For example, an element in an interface may be moved to a new location within the interface (e.g., closer to one or more of the fingers) based on the detected finger position.

Further, in certain embodiments, the controller 110 may be configured to detect which hand is holding the user device 20, based on the detected finger position. For example, the touch panel 130 sensors may detect a plurality of fingers on the left side of the user device 20 (e.g., on an edge of the display 120 or on the protective casing), and detect a single finger on the right side of the user device 20. In this exemplary scenario, the controller 110 may determine that the user is holding the user device 20 with his/her right hand because the detected grip pattern corresponds to an expected pattern when the user device 20 is held only with the right hand.

The operation key 140 may include one or more buttons or similar external control elements, which may generate an operation signal based on a detected input by the user. In addition to outputs from the touch panel 130, these operation signals may be supplied to the controller 110 for performing related processing and control. In certain aspects of the present disclosure, the processing and/or functions associated with external buttons and the like may be performed by the controller 110 in response to an input operation on the touch panel 130 display screen rather than the external button, key, etc. In this way, external buttons on the user device 20 may be eliminated in lieu of performing inputs via touch operations, thereby improving water-tightness.

The antenna 106 may transmit/receive electromagnetic wave signals to/from other external apparatuses, and the short-distance wireless communication processor 107 may control the wireless communication performed between the other external apparatuses. Bluetooth, IEEE 802.11, and near-field communication (NFC) are non-limiting examples of wireless communication protocols that may be used for inter-device communication via the short-distance wireless communication processor 107.

The user device 20 may include a motion sensor 108. The motion sensor 108 may detect features of motion (i.e., one or more movements) of the user device 20. For example, the motion sensor 108 may include an accelerometer to detect acceleration, a gyroscope to detect angular velocity, a geomagnetic sensor to detect direction, a geo-location sensor to detect location, etc., or a combination thereof to detect motion of the user device 20. In certain embodiments, the motion sensor 108 may generate a detection signal that includes data representing the detected motion. For example, the motion sensor 108 may determine a number of distinct movements in a motion (e.g., from start of the series of movements to the stop, within a predetermined time interval, etc.), a number of physical shocks on the user device 20 (e.g., a jarring, hitting, etc., of the electronic device), a speed and/or acceleration of the motion (instantaneous and/or temporal), or other motion features. The detected motion features may be included in the generated detection signal. The detection signal may be transmitted, e.g., to the controller 110, whereby further processing may be performed based on data included in the detection signal. The motion sensor 108 can work in conjunction with a Global Positioning System (GPS) section 160. The GPS section 160 detects the present position of the terminal device 100. The information of the present position detected by the GPS section 160 is transmitted to the controller 110. An antenna 161 is connected to the GPS section 160 for receiving and transmitting signals to and from a GPS satellite.

The user device 20 may include a camera section 109, which includes a lens and shutter for capturing photographs of the surroundings around the user device 20. In an embodiment, the camera section 109 captures surroundings of an opposite side of the user device 20 from the user. The images of the captured photographs can be displayed on the display panel 120. A memory section saves the captured photographs. The memory section may reside within the camera section 109 or it may be part of the memory 150. The camera section 109 can be a separate feature attached to the user device 20 or it can be a built-in camera feature.

Figure 3A:
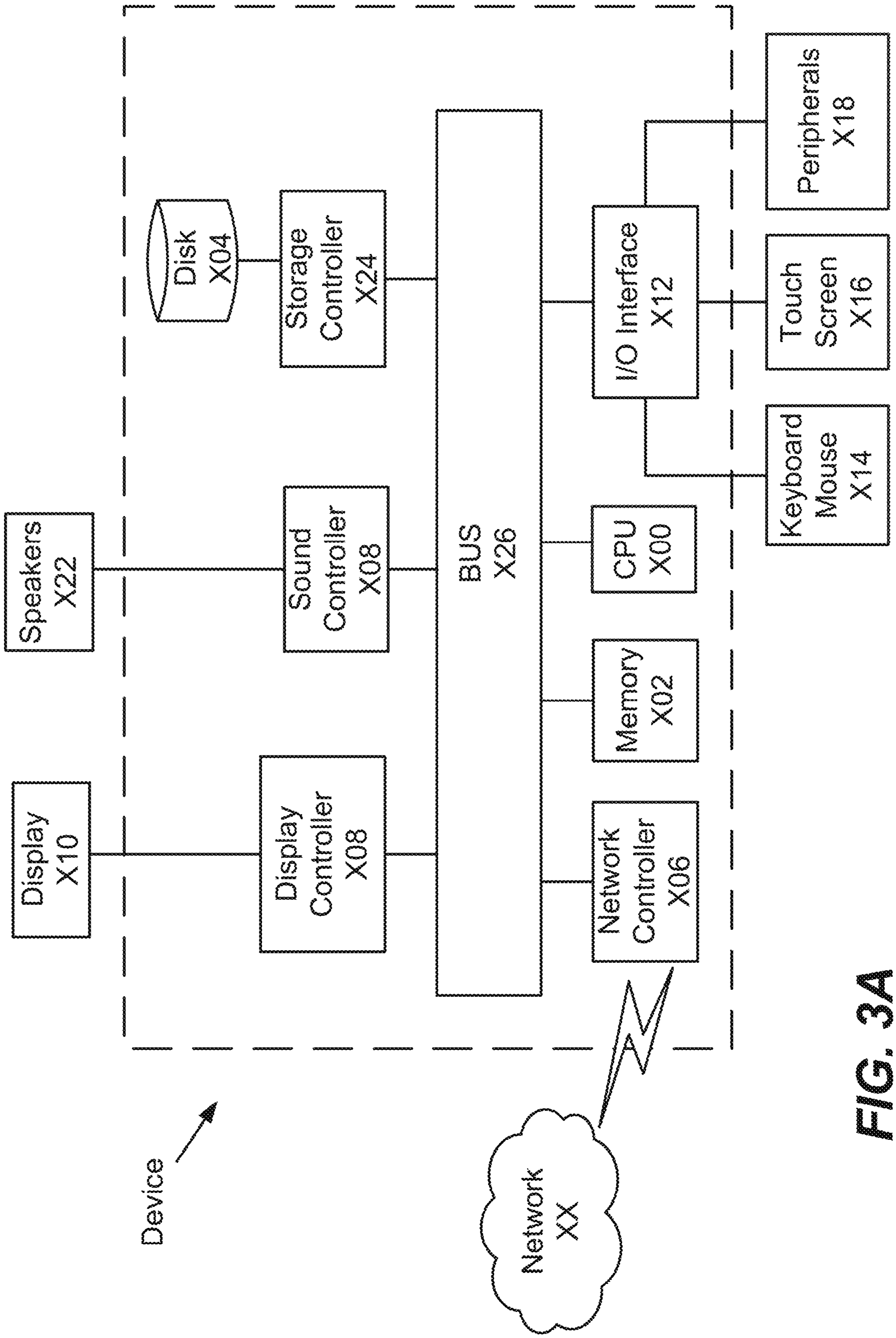
FIG. 3A shows a hardware description of a server device.

Next, a hardware description of the one or more server devices 102 according to exemplary embodiments is described with reference to FIG. 3A. In FIG. 3A, the device includes a CPU X00 which performs the processes described above/below. The process data and instructions may be stored in memory X02. These processes and instructions may also be stored on a storage medium disk X04 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the [device]communicates, such as a server or computer.

Further, the claimed advancements may be provided as a utility application, background daemon, or component of an operating system, or combination thereof, executing in conjunction with CPU X00 and an operating system such as Microsoft Windows 7, UNIX, Solaris, LINUX, Apple MAC-OS and other systems known to those skilled in the art.

The hardware elements in order to achieve the device may be realized by various circuitry elements, known to those skilled in the art. For example, CPU X00 may be a Xenon or Core processor from Intel of America or an Opteron processor from AMD of America, or may be other processor types that would be recognized by one of ordinary skill in the art. Alternatively, the CPU X00 may be implemented on an FPGA, ASIC, PLD or using discrete logic circuits, as one of ordinary skill in the art would recognize. Further, CPU X00 may be implemented as multiple processors cooperatively working in parallel to perform the instructions of the inventive processes described above.

The device in FIG. 3A also includes a network controller X06, such as an Intel Ethernet PRO network interface card from Intel Corporation of America, for interfacing with network XX. As can be appreciated, the network XX can be a public network, such as the Internet, or a private network such as an LAN or WAN network, or any combination thereof and can also include PSTN or ISDN sub-networks. The network XX can also be wired, such as an Ethernet network, or can be wireless such as a cellular network including EDGE, 3G and 4G wireless cellular systems. The wireless network can also be Wi-Fi, Bluetooth, or any other wireless form of communication that is known.

The device further includes a display controller X08, such as a NVIDIA GeForce GTX or Quadro graphics adaptor from NVIDIA Corporation of America for interfacing with display X10, such as a Hewlett Packard HPL2445w LCD monitor. A general purpose I/O interface X12 interfaces with a keyboard and/or mouse X14 as well as a touch screen panel X16 on or separate from display X10. General purpose I/O interface also connects to a variety of peripherals X18 including printers and scanners, such as an OfficeJet or DeskJet from Hewlett Packard.

A sound controller X20 is also provided in the [device], such as Sound Blaster X-Fi Titanium from Creative, to interface with speakers/microphone X22 thereby providing sounds and/or music.

The general purpose storage controller X24 connects the storage medium disk X04 with communication bus X26, which may be an ISA, EISA, VESA, PCI, or similar, for interconnecting all of the components of the device. A description of the general features and functionality of the display X10, keyboard and/or mouse X14, as well as the display controller X08, storage controller X24, network controller X06, sound controller X20, and general purpose I/O interface X12 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

Figure 3B:
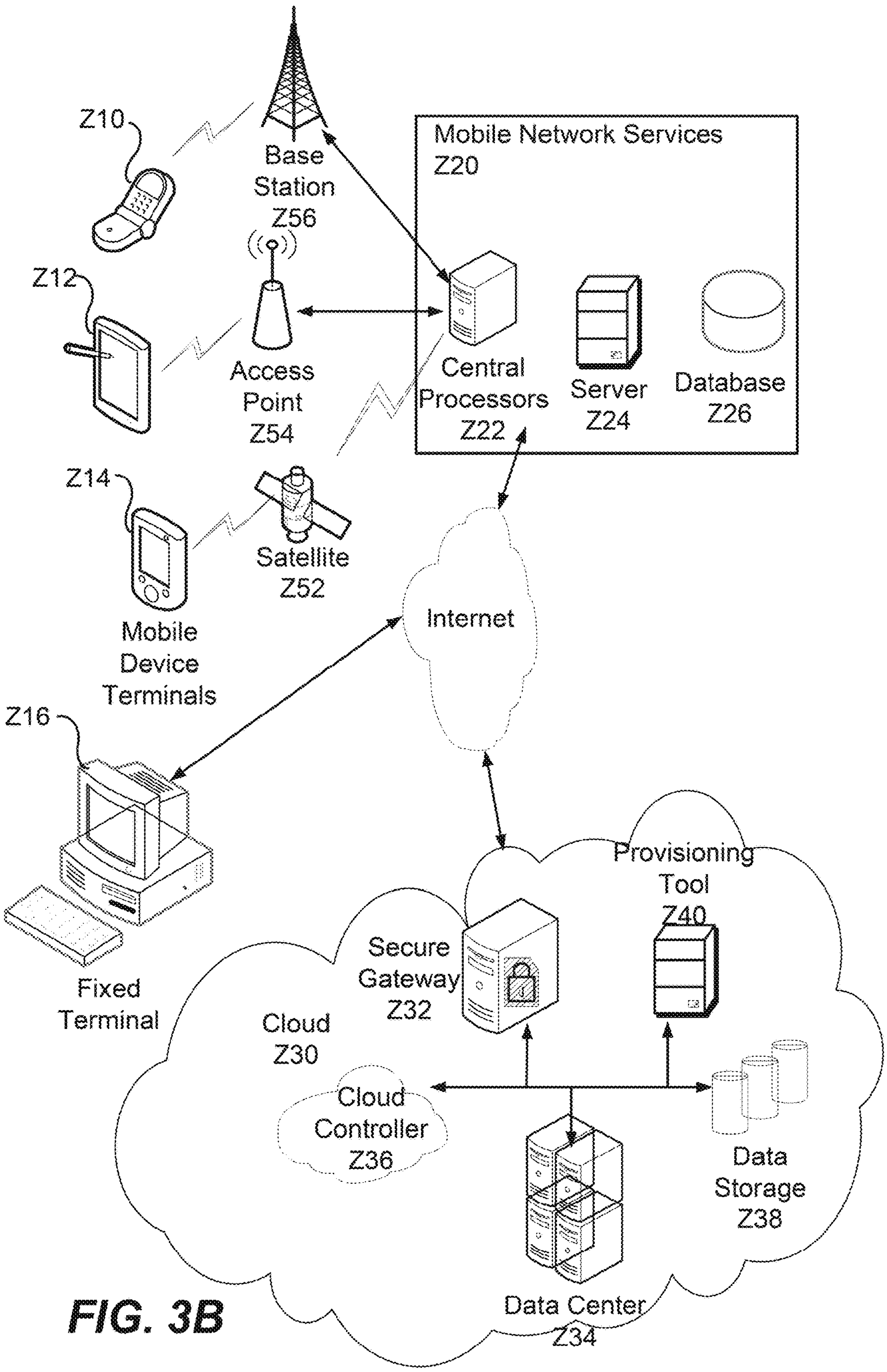
FIG. 3B shows distributed components in a network.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 3B, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

[User Data Collection]

Figure 4:
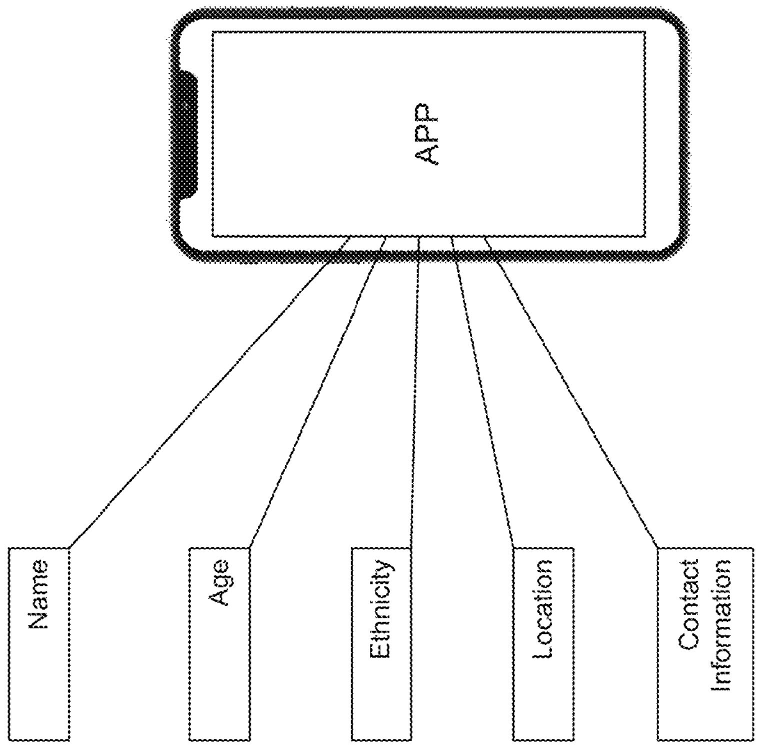
FIG. 4 shows the personal information that is received by the application from the user.
Figure 5:
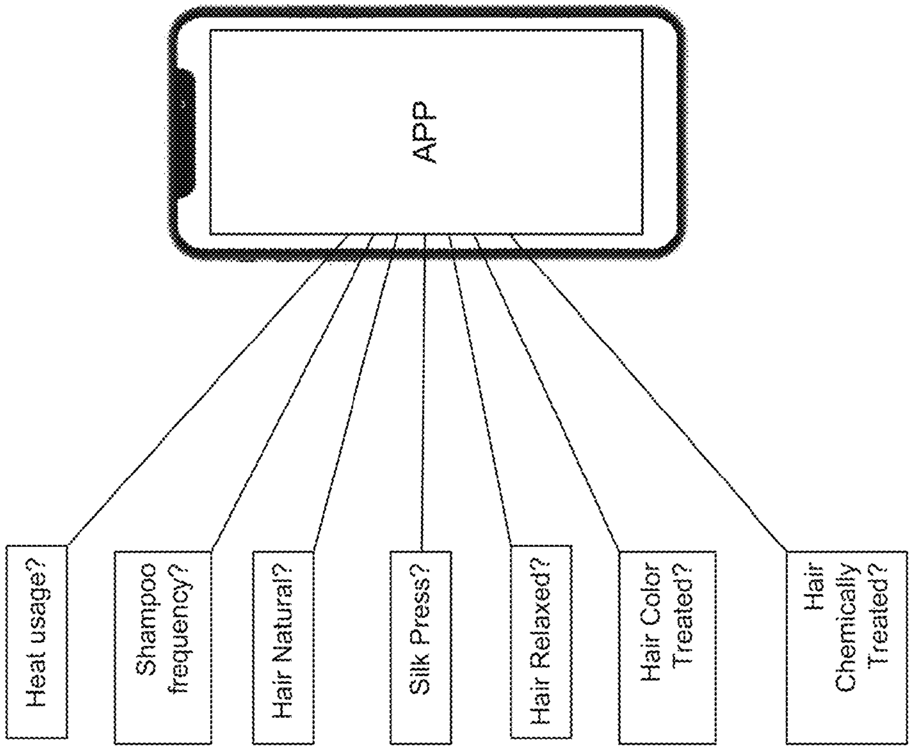
FIG. 5 shows information on personal habits that is received by the application from the user.

1. User Information Gathering on Current Hair Condition: Self-Described Information FIGS. 4-5 show the types of descriptive information that is received by the application from the user with regard to their current hair condition. The information may include one or both of image information and descriptive information.

For instance, as shown in FIG. 4, as personal information, the application collects one or more of the user's name, age, ethnicity, location, and contact information.

As shown in FIG. 5, the user may also provide information on their current hair care habits, which may be referred to as their "current hair journey." It can be seen that this information includes one or more of the following items.

Whether or not the user uses heat in treating their hair
The frequency of using shampoo and/or conditioning products
Whether the user uses a silk press treatment
Whether the user leaves their hair relaxed
Whether the user's hair is color-treated
Whether the user's hair is chemically treated.

Figure 6:
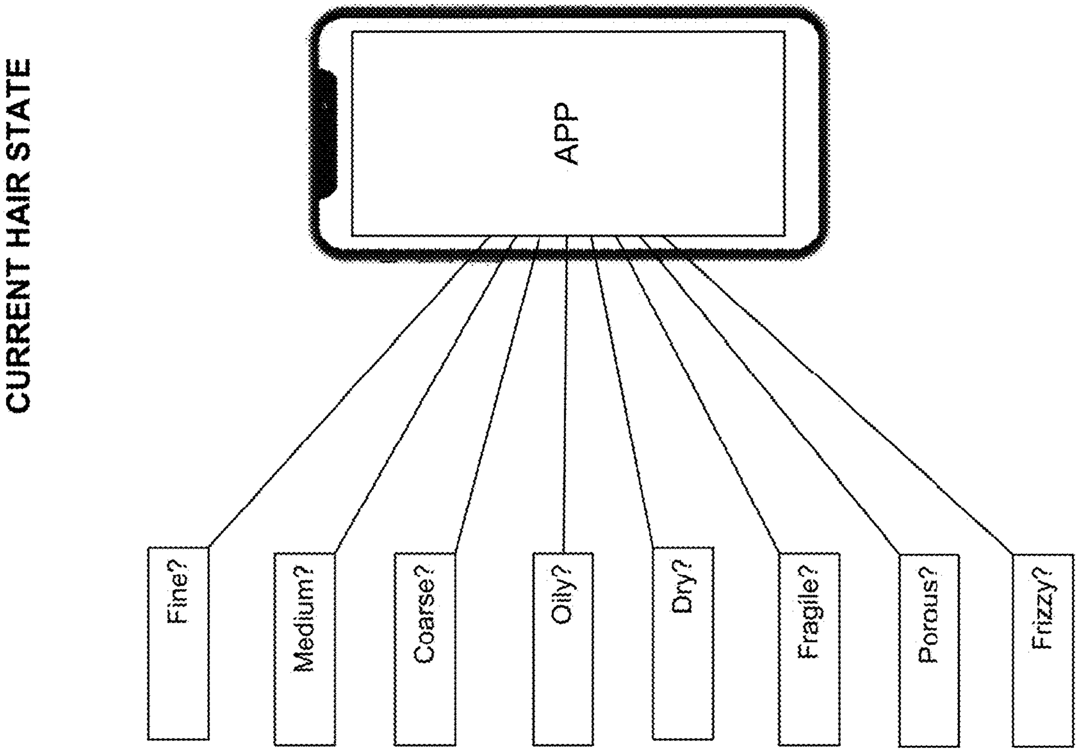
FIG. 6 shows the perceived current hair state that is received by the application from the user.

As shown in FIG. 6, the user may also provide information on their perceived current hair state. For instance, the user may self-describe their hair as one or more of being fine, medium, coarse, oily, dry, fragile, porous, or frizzy.

The user may also provide information on whether their hair has different types of curls or characteristics at different regions of the hair. For instance, while one curl type may be present at the most visible portions of the hair, another curl type may be present at a less visible region such as the back of the neck. A conventional AI hair imaging system would not take into account this type of information and it would likely have to be provided as user information.

Figure 7B:
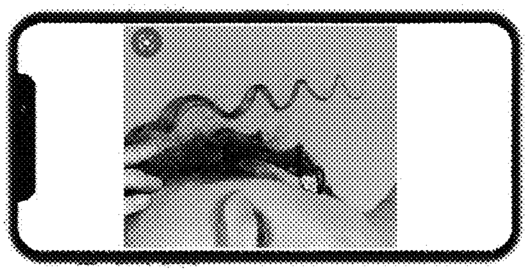
FIG. 7B shows that a user may take a selfie image of a portion of their hair.
Figure 7A:
FIG. 7A shows that a user may take one or more "selfie" images of their hair.

FIG. 7A shows that a user may take one or more "selfie" images of their hair. Specifically, the user may take selfie picture, a 360° selfie picture, or a series of photos at different angles using the smartphone camera capability.

In a preferred embodiment, as shown in FIG. 7B, as the user should take the selfie-image of the portion of the hair that embodies the curl pattern of their hair, such as the side of the hair, or if possible a view from the back of their hair. The image is preferably taken against a white background.

[Desired Look/Benefits Information]

Figure 8:
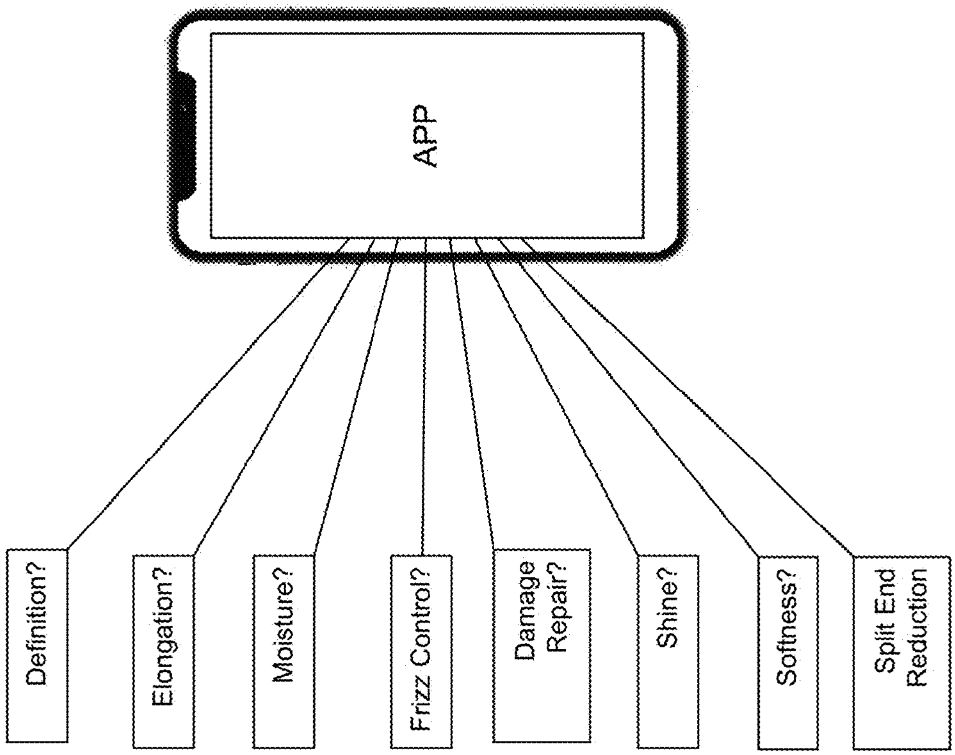
FIG. 8 shows the types of descriptive information that is received by the application from the user with regard to their desired (target) look.

FIG. 8 shows the types of descriptive information that is received by the application from the user with regard to their desired (target) look.

The user can provide their target look using both words and/or images. As shown in FIG. 8, the user may input descriptive terms regarding the desired benefits, such as achieving more definition, elongation, moisture, frizz control, damage repair, shine, softness, or split end reduction.

Figure 9:
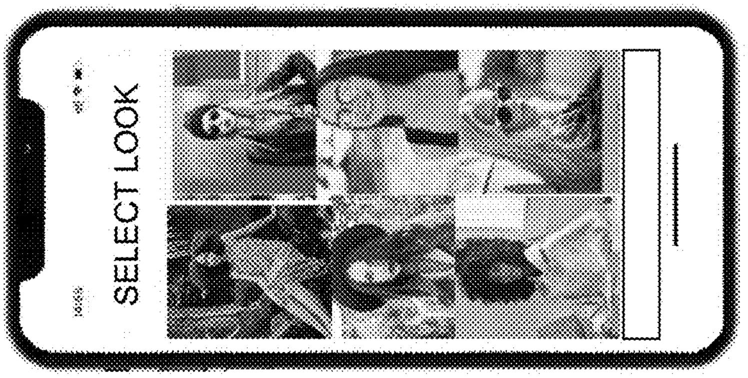
FIG. 9 shows that the user may input one or more images indicative or their desired "end look."

As shown in FIG. 9, the user may input one or more images indicative or their desired "end look." This may be done in conjunction or alternatively from the descriptive terms provided by the user. For instance, the user may select images taken from the Internet. The images may be provided from a plurality of image displayed for the user directly within the application itself. These pictures may be pre-associated textual descriptors, such as representing a look with one or more Alternatively, the images may not be pre-associated with textual descriptors, and image analysis may be performed on the image to determine the characteristics of the model's hair in the image.

[Curl Diagnosis]

After collecting the description information and the image information from the user, the application will cause a curl diagnosis to be performed. Part of the curl diagnosis involves performing image analysis to determine the type or curl pattern of the user along with other attributes, such as texture, damage level, shine level, dryness, and color.

Figure 10:
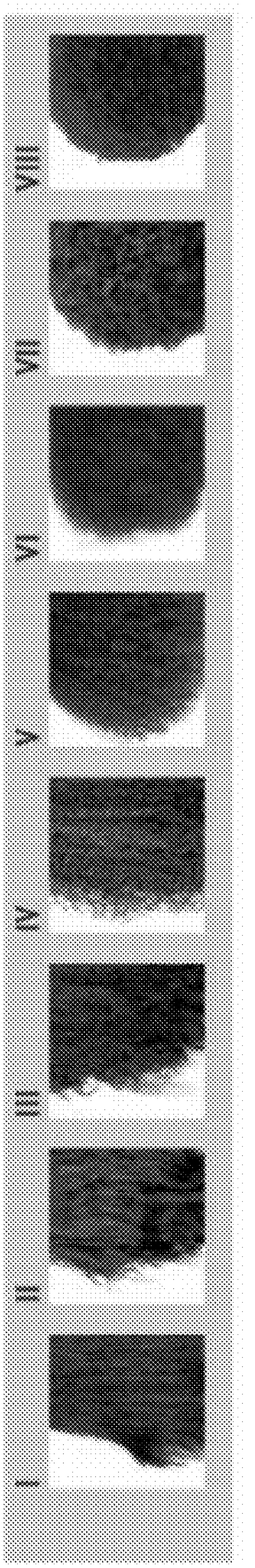
FIG. 10 shows a chart of different types of curl patterns according to an embodiment.

FIG. 10 shows a chart of different types of curl patterns according to an embodiment. In this example, there are eight different types of curl patterns, which may represent curl patterns that are wavy, curly, or coily. There are different methods of performing image analysis.

One method is to detect features in an image that indicate a certain curl pattern. For instance, an angle in the hair pattern may be detected. Because of the contrast of the user's hair in the image against a white background, the pixels of the certain color are detected and the average curl is plotted on a 2D scatter plot. To facilitate this step, the white balance image may be optimized such that the white balance of the picture to facilitate the detection black versus white contrast. The system can also automatically detect the percentage of black versus white within the white background.

Figure 11:
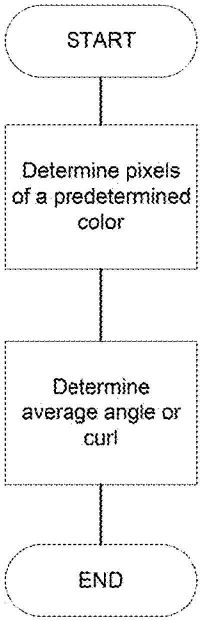
FIG. 11 shows a method of automatically detecting the percentage of black versus white within the white background.

A method according to this type of detection is shown in FIG. 11. In step 1101, the system determines pixels of a predetermined color, which may be any non-white color assuming that the image is taken against a white background. In step 1102, the average angle and curl is measured.

The average angle and curl of the hair is measured using linear regression. Specifically, the pixels in an "expected maximum" region are labelled in red and fit with polynomial (degree=2) regression. Using a couple heuristics for which side of the parabola to pick, it measures from one of the tips of the parabola to the base. The heuristics are based on which side of the parabola has more data points and the concavity of the curve. This technique is described in more detail in U.S. Pat. No. 10,929,993, and is hereby incorporated by reference.

Another method is to use deep learning or machine learning to train a model to determine a curl pattern in the images. In this embodiment, the system implements one or more convolutional neural networks (CNNs), the models for which may be trained using open source datasets or crowd-sourced data sets, as explained below. Other machine learning techniques may be used in conjunction with the present invention including, but not limited to, decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning and learning classifiers. Additional techniques described in U.S. Pat. Nos. 8,442,321, 9,015,083, 9,536,293, 9,324,022, and U.S. PG Publication No. 2014/0376819 A1, all of which are incorporated herein by reference, may be used with the present invention. In the descriptions that follow, it will be assumed that machine learning logic implements a convolutional neural network, although the present invention is not so limited. Those having skill in artificial intelligence will recognize numerous techniques that can be used in conjunction with the present invention without departing from the spirit and intended scope thereof.

Figure 12:
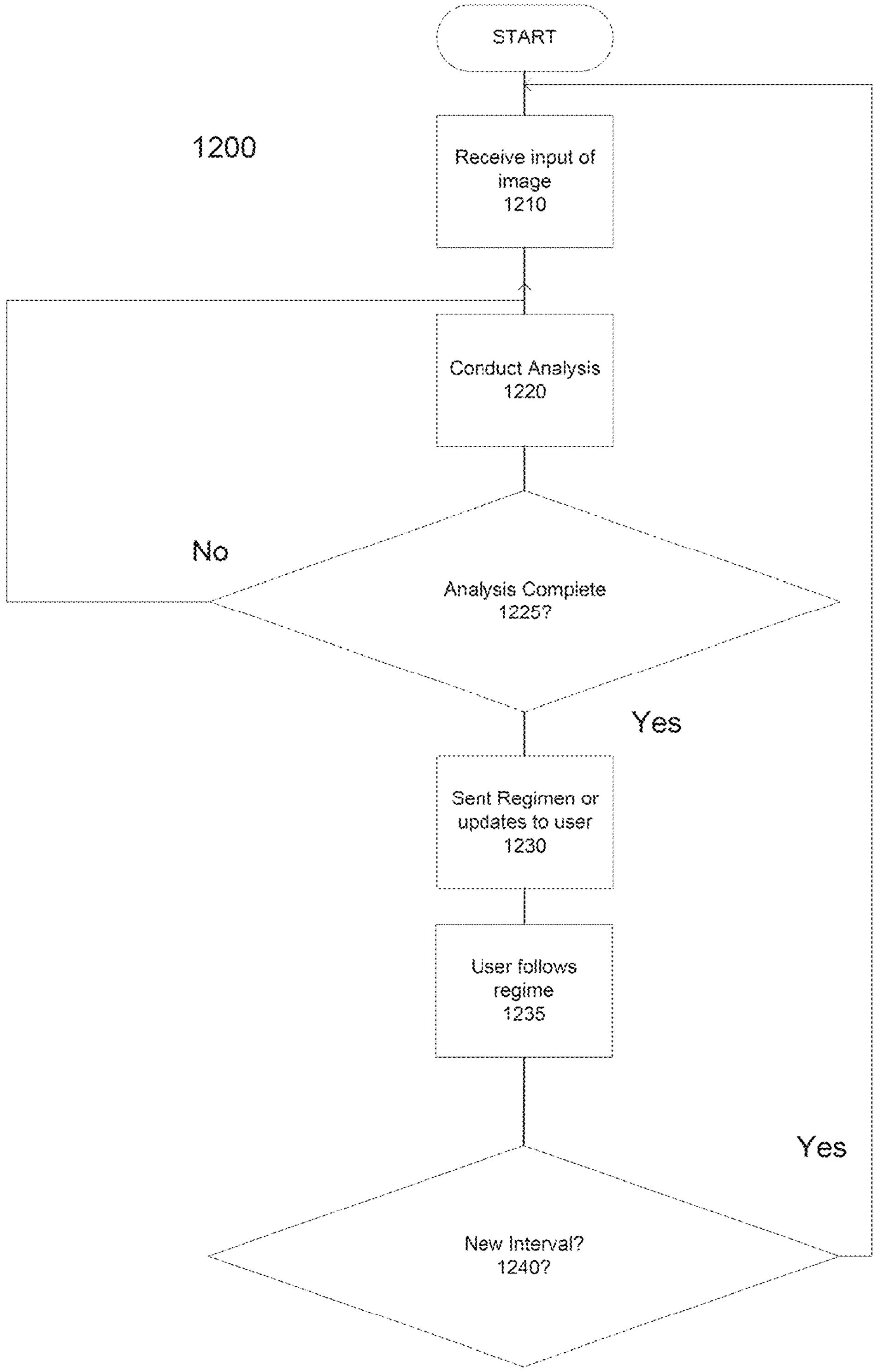
FIG. 12 is a flow diagram by which an example interaction with an embodiment of the invention can be explained.

FIG. 12 is a flow diagram by which an example interaction with an embodiment of the invention can be explained. The interaction of FIG. 12 is in no way intended to be limiting. The description of FIG. 12 is intended to illustrate functionality of the configuration illustrated in FIG. 1. Further features of the invention, beyond those described with reference to FIG. 12, will be discussed below.

In operation 1210, the captured selfie image of the user is received

In operation 1220, image analysis and machine learning is conducted to analyze the user's skin from the images. The system may perform analyses that determine, among other things, a type of curl pattern, a texture of the hair, a damage level of the hair, a shine level of the hair, a dryness of the hair, and a color of the hair. Other conditions of the hair may be determined by the system. Further details of the analyses are provided below. Once the analyses have been completed, as determined in operation 1225, process 1200 may transition to operation 1230, whereby the analyses results and the prescribed regimen (products and routines) and/or updates to the regimen are sent to the user via an interface of the application.

In operation 1225, it is determined whether the analysis is complete and, responsive to a positive determination thereof, process 1200 may transition to operation 1230, whereby the application sends a recommended regimen or updates to the user in operation 1230. The user may follow the regimen as indicated in operation 1235 and, in operation 1240 it is determined whether a new interval has commenced. If so, process 1200 reiterates from operation 1210. The system may access calendars and timers (as well as GPS) onboard the client device as well as access to network-accessible calendars on a network. Accordingly, once a week, say, the application may remind the user to take a picture of his/her hair, i.e., remind him of the new interval. Over time, the system can determine from the images taken at each interval whether the recommended regimen is working and, if not, the system may revise the regimen, e.g., change a product, recommend further lifestyle changes, make a specialist appointment, etc.

Figure 13:
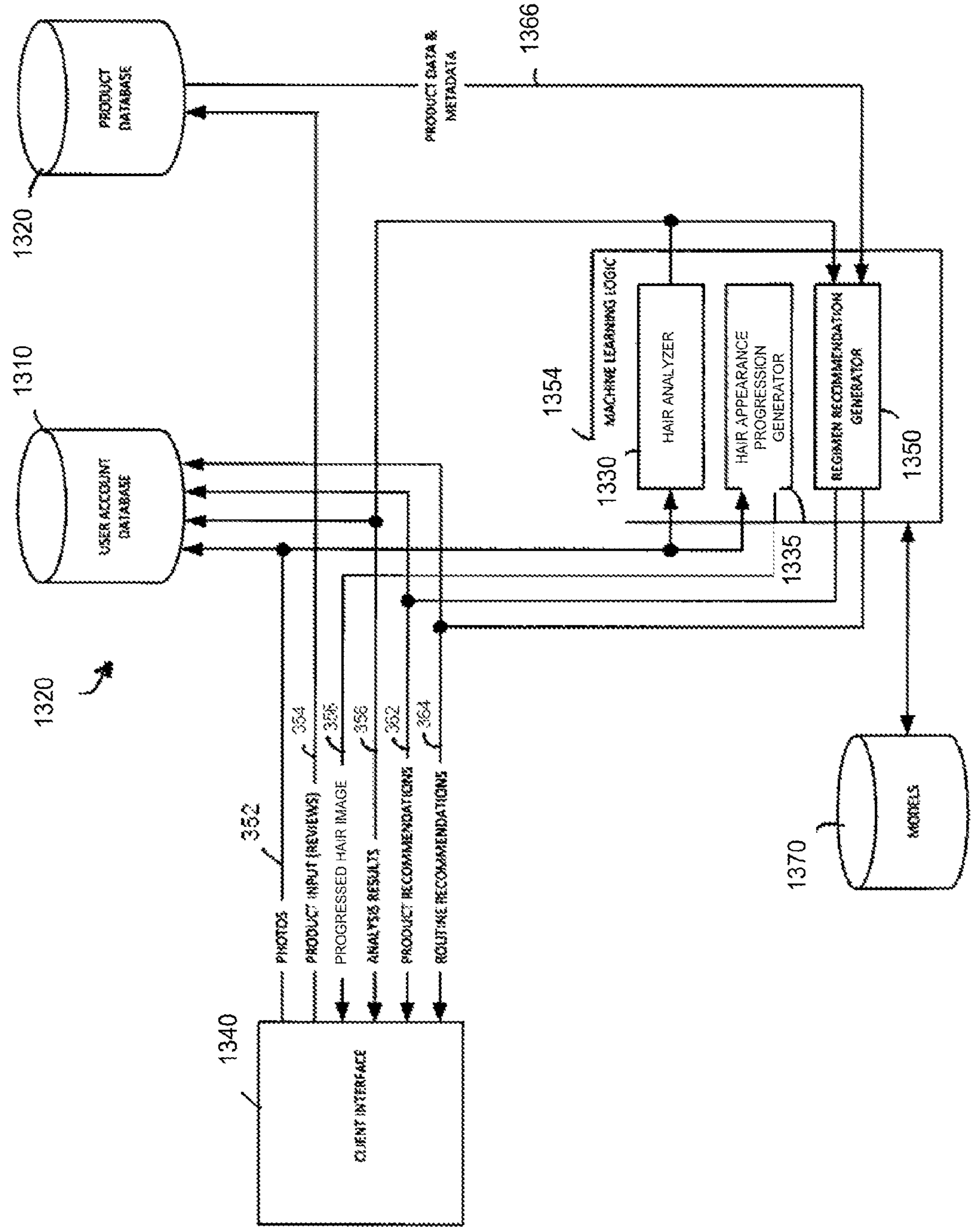
FIG. 13 is a diagram of data flow between an exemplary client interface 1340 (i.e., the application) and services of a service platform 1320.

FIG. 13 is a diagram of data flow between an exemplary client interface 1340 (i.e., the application) and services of a service platform 1320. It should be noted that, in FIG. 13. As illustrated in FIG. 13, the machine learning logic 1354 may comprise a hair analyzer 1330, facial appearance progression generator 335 and a regimen recommendation generator 1350 and may be communicatively coupled to a user account database 310 and a product database 320. Machine learning logic 1354 may train and utilize machine learning models 1370 to recommend regimens and to track the progress of the user under the regimen. As those skilled in machine learning will attest, training may involve selecting a set of features, e.g., a type of curl pattern, a texture of the hair, a damage level of the hair, a shine level of the hair, a dryness of the hair, and a color of the hair, and assigning labels to image data that reflects the presence or prominence of those features. The assigning of labels may be performed by a subject matter expert or, as explained below, through crowdsourced data. Taking the assigned labels as ground truth, machine learning logic 1354 may configure models 1370 to predict the degree to which the features are present in a test image, which may change over time. The present invention is not limited to a particular model representation, which may include binary models, multiclass classification models, regression models, etc.

Exemplary user account database 1310 contains the data of all users of system 100 in a secure manner. This includes user profile data, current and past user photos 352 for each user, current and past hair analyses 358 for each user, current and past product recommendations 362 and current and past routine recommendations 364 for each user.

Exemplary product database 1320 contains the data of different products that can be used in a regimen. Product database 1320 may contain records reflecting the product names, active and inactive ingredients, label information, recommended uses, and so on. In certain embodiments, as illustrated as product input 354, the user (and other users of system) may provide feedback on different products and may enter products not already in product database 1320. The present invention is not limited to particular products that can be entered in product database 1320.

Hair analyzer 1330 is constructed or is otherwise configured to classify various hair analyzer conditions or artifacts from imagery of a user's hair using machine learning techniques over models 1370. In certain embodiments, photographic images 352 of a user's hair are provided to hair analyzer 1330 for analysis. Hair analyzer 330 may implement image preprocessing mechanisms that include cropping, rotating, registering and filtering input images prior to analysis. After any such preprocessing, hair analyzer 1330 may apply models 1370 to the input image to locate, identify and classify characteristics of the user's hair.

Hair appearance progression generator 1335 may operate on the user's hair images to portray how the user's face would appear sometime in the future. Such progression may be in age, for which age progression techniques may be deployed, or may be in appearance resulting from adherence to a regimen. A progressed image 356 may be provided to the user through client interface 1340.

Regimen recommendation generator 1350 may operate on analysis results 358 obtained from hair analyzer 1330 towards prescribing a regimen to the user. Models 1370 may be trained to predict what products and routines (treatment, cosmetic and lifestyle recommendations, etc.) would be effective in meeting the user's goal with regard to hair characteristics identified in the hair analysis. Regimen recommendation generator 1340 may format the analysis results 358 of hair analyzer 1330 as a query into, for example, product database 1320 based on knowledge encoded on models 1370. In response, product database 1320 may return product data and metadata 1366, and product recommendations 362 and routine recommendations 364 may be provided to client interface 1340.

As indicated above, training of models 1370 may be achieved by labeling of image data by an expert. However, in lieu of an expert, certain embodiments of the invention utilize crowdsourced data as training data.

Figure 14:
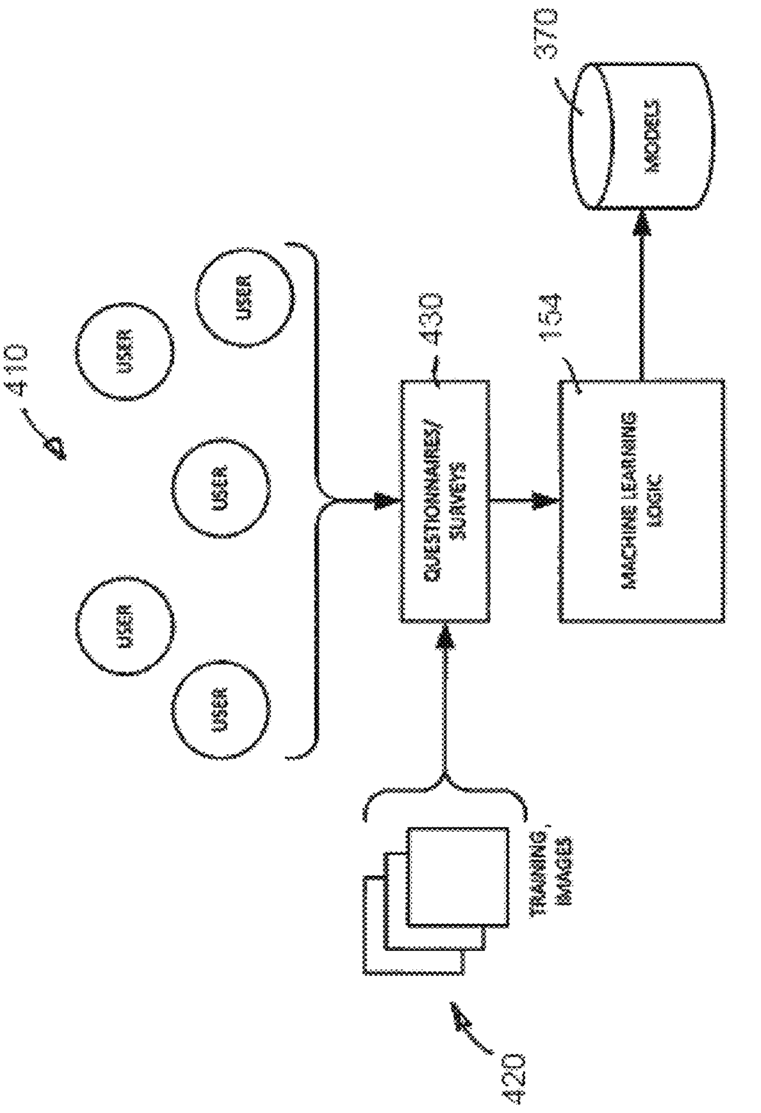
FIG. 14 is a diagram of an embodiment that uses crowdsourced data as training data.

FIG. 14 is a diagram of such an embodiment of the invention. During training, users 410 are presented a set of training images 420 over which they are asked to characterize curl patterns, and/or hair features. In one embodiment, the curl pattern scale shown on FIG. 10 is used with which users can rate the type of curl pattern. For example, each of users 410 (over time) are presented a large number of images and is walked through a set of questions regarding features of the person in the image. Using the scale, each user 410 is asked to select one of the curl types. The answers to the questions may serve as labels used for training machine language logic 1340.

Figure 15:
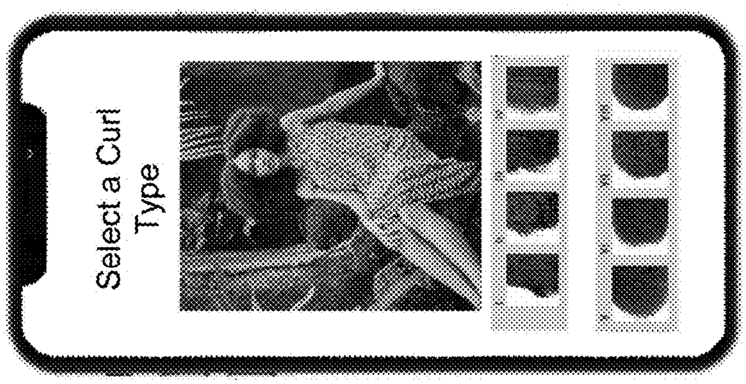
FIG. 15 shows an example in which the application presents a photograph of a model and asks the user to determine which curl type is shown in the image.

Referring to FIG. 15, there is illustrated an example 1500 in which the application presents a photograph of a model 1510 and ask the user to determine which curl type, from a plurality of curl types 1520 is shown in the image.

Figure 16:
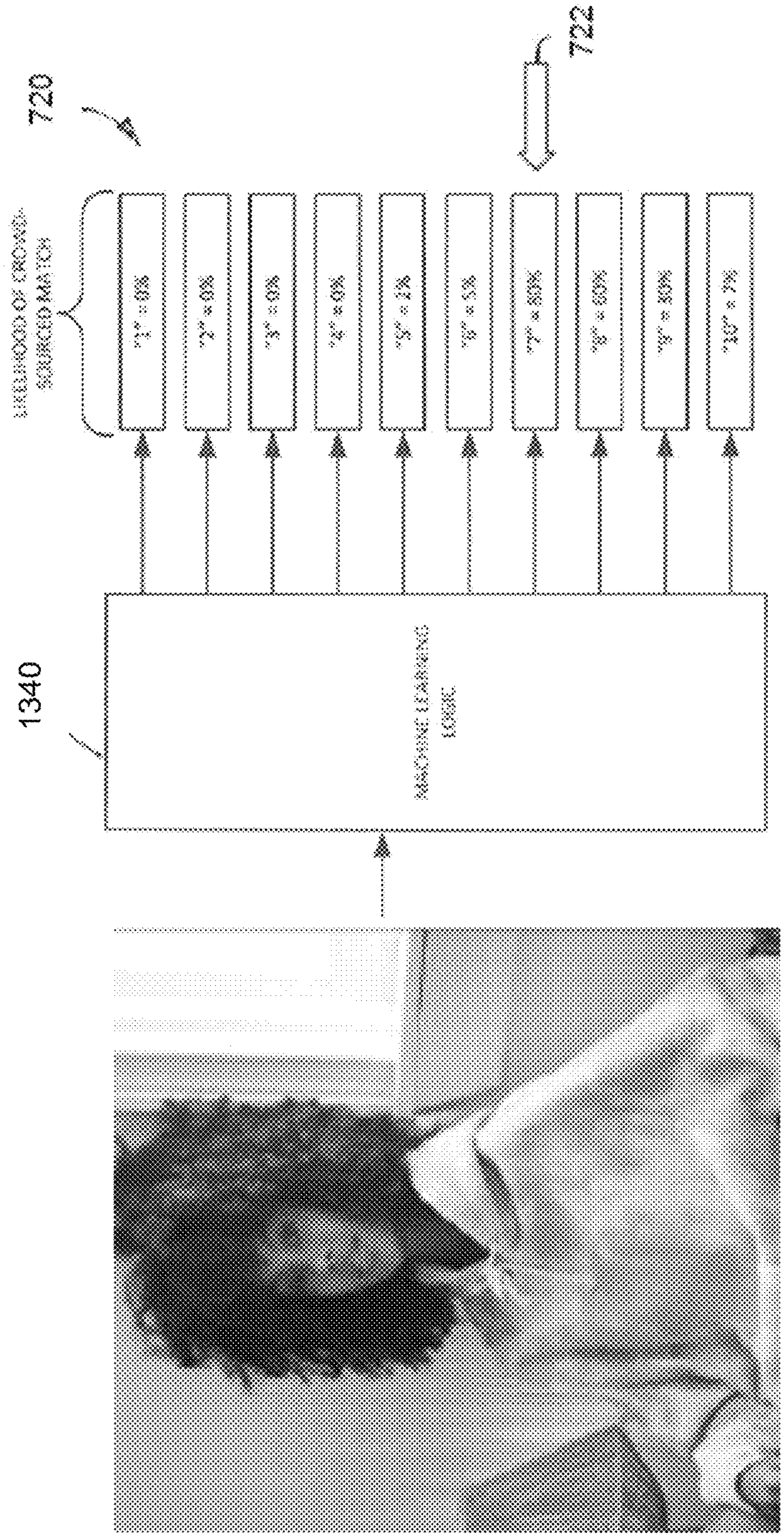
FIG. 16 illustrates an example test operation in accordance with the crowdsourced training embodiment.

FIG. 16 illustrates an example test operation in accordance with the crowdsourced training discussed above. A test image 710, i.e., a user's own image, may be presented to machine learning logic 154, which analyzes the image per the models trained on the crowdsourced data 720. As illustrated in the figure, machine learning logic 1340 estimates that 80% of people surveyed would rate the user's curl pattern as a type #7 as indicated at 722. Accordingly, machine learning logic 1340 may use the curl type #7 as a piece of input data when making recommendations as will be described below.

The user's textual descriptors can be used to aid the curl diagnosis as a further input into the model. For instance, the inclusion of a user's textual word describing their own hair in combination with visual features in the image of their hair will contribute to weighting the probability of an identified curl pattern in the image.

The machine learning system described above may further include a curl identification component including circuitry configured to generate a pixel-wise prediction score for a presence or absence of hair curls and to predict a score for a presence or absence of a specific curl pattern in an image using one or more convolutional neural network image classifiers. In this method, generating the predicted score for the presence or absence of the specific curl pattern in the image includes generating a score indicative of the presence or absence of a combination of one or more of coily hair pattern, curly hair pattern, kinky hair pattern, wavy hair pattern, or straight pattern. The predicted score for the presence or absence of the specific curl pattern in the image may include a score indicative of the presence or absence of coily hair pattern, curly hair pattern, kinky hair pattern, wavy hair pattern, or straight pattern. The predicted score for the presence or absence of the specific curl pattern in the image includes a score indicative of the presence or absence of a curl pattern from a plurality of predetermined curl patterns on a curl scale.

A curl assessment component may also be provided that includes circuitry configured to generate a user selectable menu that permits a user to choose from a plurality of hair characteristics and curl pattern images and to generate user hair assessment information responsive to one or more inputs associated with least one of the prediction score for a presence or absence of hair curls and to the predict a score for a presence or absence of a specific curl pattern.

A method may also be provided for applying a convolutional neural network image classifier to a user image to obtain pixel-wise prediction scores for presence or absence of hair curls and hair curl types, and generating a virtual representation of a portion of the user image and a predicted hair curl type based on the prediction scores for presence or absence of hair curls and hair curl types.

A computer-implemented method may also be provided of training a neural network for hair curl detection. This method includes collecting a set of digital coily hair patter images, curly hair pattern images, kinky hair patter images, or wavy hair pattern images from a data store; applying one or more transformations to each digital hair image to create a modified set of digital hair images; creating a first training set comprising the collected set of digital hair images, the modified set of digital hair images, and a set of digital non-hair curl pattern images; training a neural network in a first stage using the first training set; creating a second training set for a second stage of training comprising the first training set and digital non-hair curl images that are incorrectly detected as hair curl pattern images after the first stage of training; and training the neural network in a second stage using the second training set.

[Curl Treatment or Product Recommenation]

While the above process describes how the system performs a curl diagnosis, the curl diagnosis is further combined with an input of a user's desired look or benefit to obtain a product or treatment recommendation.

As shown in FIG. 8 the user inputs the desired benefit they are seeking from the application, or as shown in FIG. 9, the user made a selection of a "look" they are seeking.

Figure 17:
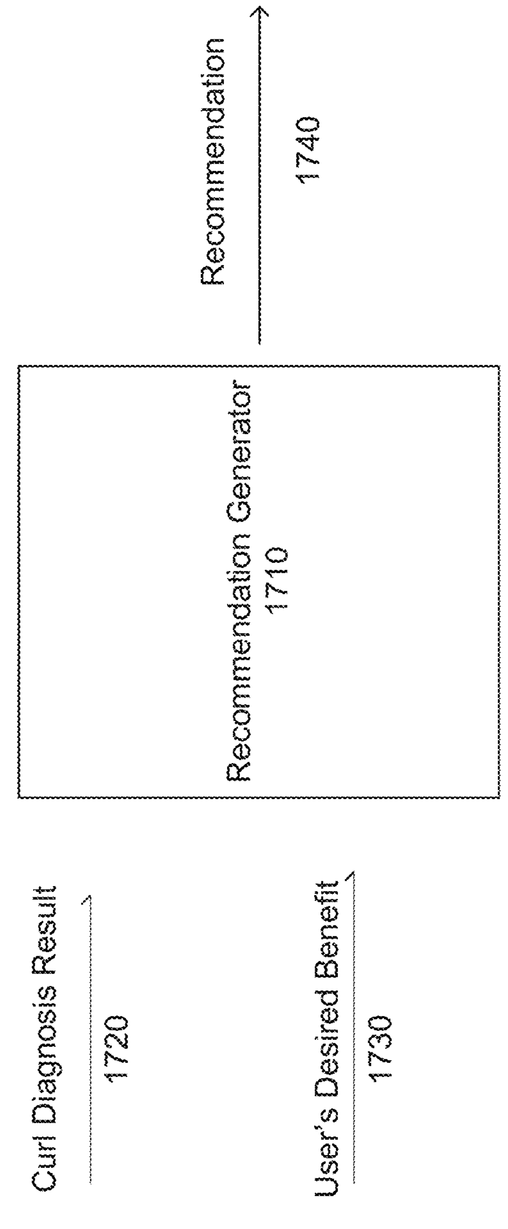
FIG. 17 shows an embodiment of a recommendation generator.

As shown in FIG. 17, functional component called the recommendation generator 1710 takes the input of the curl diagnosis 1720 and the user's desired benefit 1730, and provides a recommendation 1740 as an output.

Different methods for generating a recommendation are described below.

Table Look-Up

As a first method, a look-up table may be used which includes predetermined combinations of curl diagnosis and desired benefit in association with a predetermined output of a recommendation of a product or treatment.

Figure 18A:
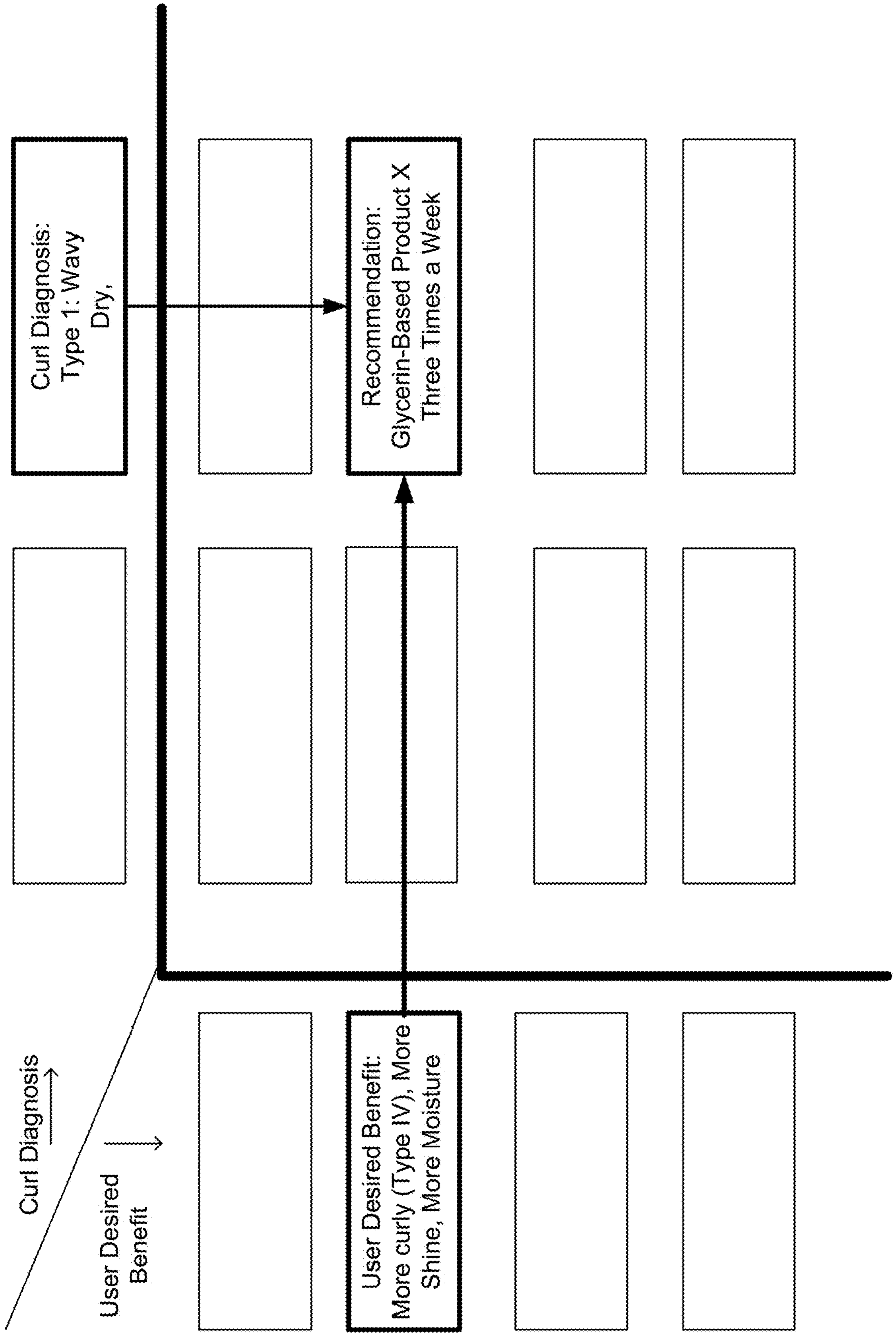

FIG. 18A shows an example of an entry in a look-up table as described above. A matrix style of table is shown where the curl diagnosis possibilities populate one look-up axis and the user desired benefits populate the opposing look-up axis. Based on the inputs received by the recommendation generator 1710, an intersection of the inputs will lead to the recommendation to be generated. While this example is simplified, the curl diagnosis could further include other assess characteristics of the user's hair as described above, and the user desired benefits could include further characteristics as well. An increase in the number of types of characteristics contained in the input data will obviously require an expanded look-up table. The type of look-up table is not limited to the type shown in FIG. 18B. The table itself can be manually generated based on expert input.

For instance, FIGS. 18B and 18C show expert information that maps a user's curl type to other characteristics, pain points, and recommendations for treatment. It is evident how this information can be used to complete the look-up table in FIG. 18A. For reference, a "zig-zag" type of hair means that the strands make a zigzag shape, not a curl or a wave. "Coily" hair is when each of the strands form tight coils. It's very versatile but can be fragile—especially if the strands are fine—because it may have a thin external layer. "Curly" hair strands cluster together and wind around themselves in a spiral or looser curl shape. This texture needs plenty of moisture to encourage a defined pattern, but a little frizz can give it personality. "Wavy" hair is when strands curve or form an "S" shape.

A second method to create the look-up table is to generate a recommendation based on machine learning. In this case, a collection of "before and after" images may be used in conjunction with a label of treatment and/or product that was used to teach a machine on what products or treatment methods lead to certain results. The images may be associated with textual descriptors, so as those provided by the user in describing their current hair condition and their desired benefits. This can be used to create a model that can be continuously updated with new training data as it is collected.

Figure 19:
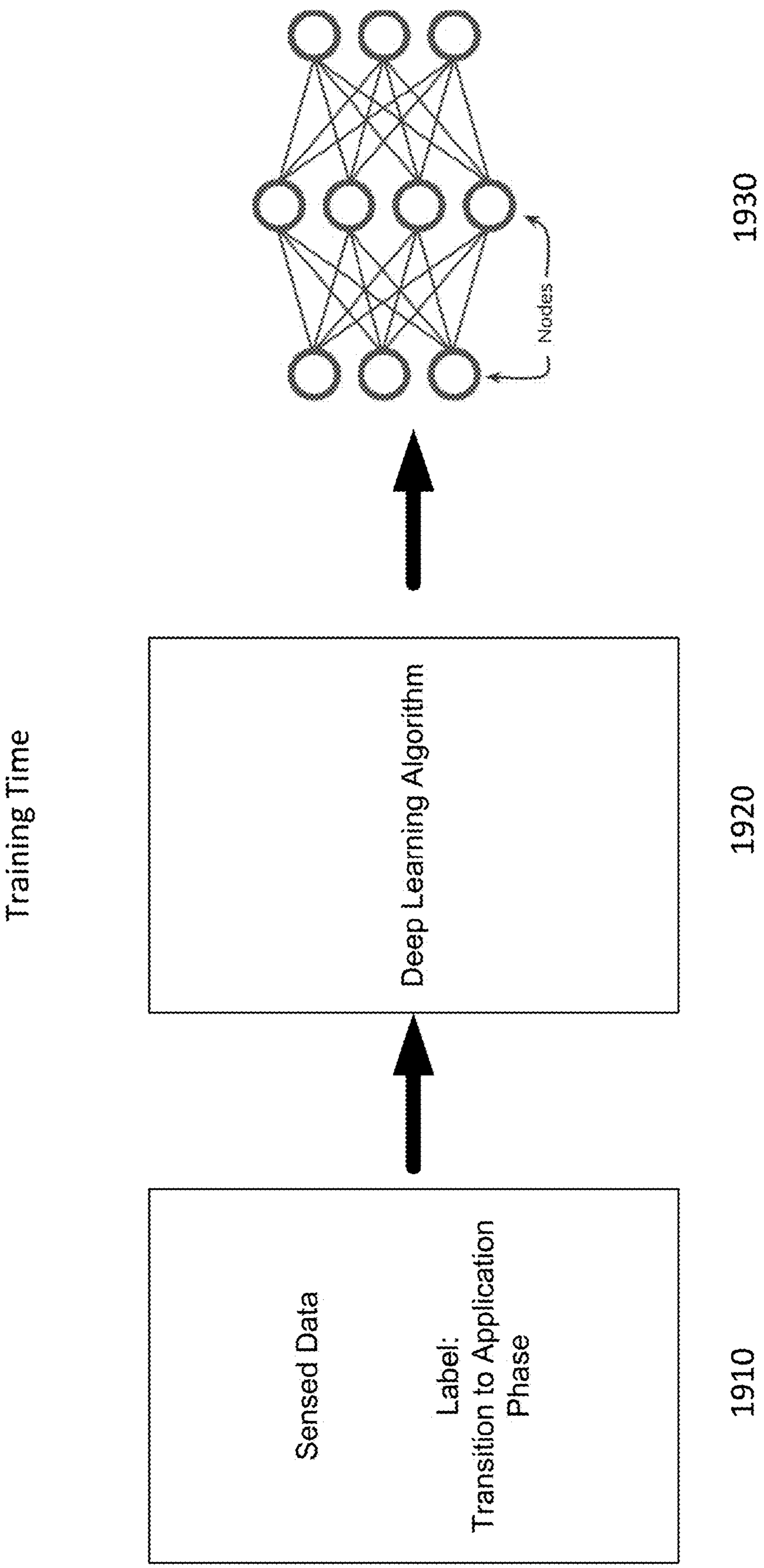
FIGS. 19-20 show details regarding how deep learning is performed to cause the smartphone app (or the cloud platform) to estimate a recommendation for a user.
Figure 20:
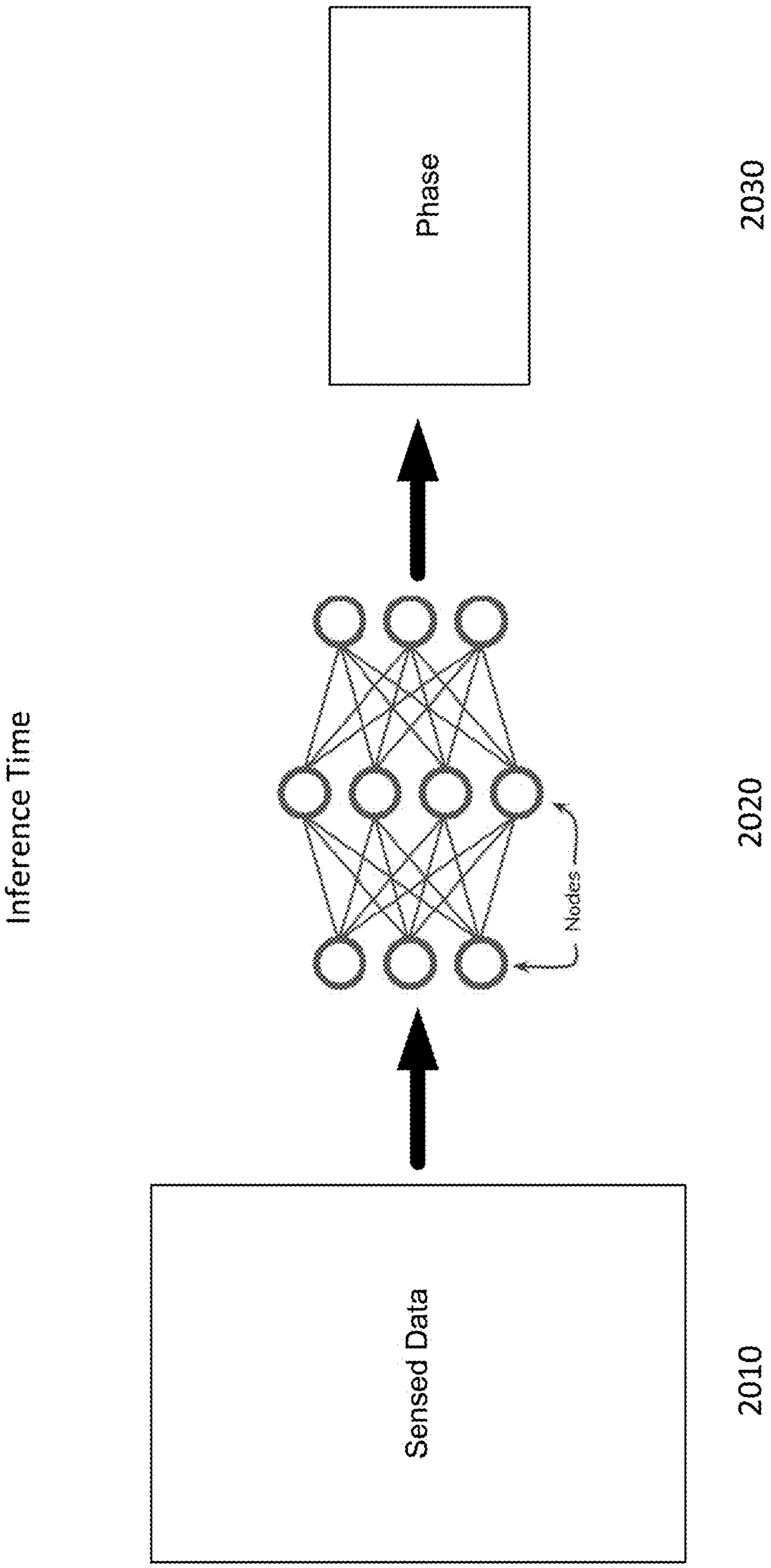

FIGS. 19-20 shows additional details regarding how deep learning is performed to cause the smartphone app (or the cloud platform) to estimate a recommendation for a user. In FIG. 19, training is performed for the deep learning model. The inputs are provided at stage 1910, where pictures (which could be 360 video selfies or picture selfies) are input along with text descriptors and a label. Since this is the training phase, actual before and after pictures of users may be used showing the originally diagnosed curl pattern and the resulting curl pattern as an image pair. Additionally, the users' self-perceived words describing their curls and the textual descriptors of their desired benefits can be input as a text pair. Finally, the "label" give to the inputted data may be the product and/or treatment which achieved the desired result.

The inputs are provided to a deep learning algorithm in step 1920. The deep learning algorithm used may be based on available software as known in the art, such as TensorFlow, Keras, Mxnet, Caffe, or Pytorch. The result of the labeled training will be a neural network at step 1940. The neural network created includes nodes of each layer are clustered, the clusters overlap, and each cluster feeds data to multiple nodes of the next layer.

FIG. 20 shows the usage of the deep learning model after training has reached an adequate level. This is referred to as "inference time" since recommendation will be inferred from input data without a label. It can be seen that the input stage does not include a label. Additionally, the image pair includes the user's inputted selfie image and the user's selected image within the application. These inputs are fed to the neural network which will provide an output of a product and treatment recommendation.

[Types of Output]

Figure 21:
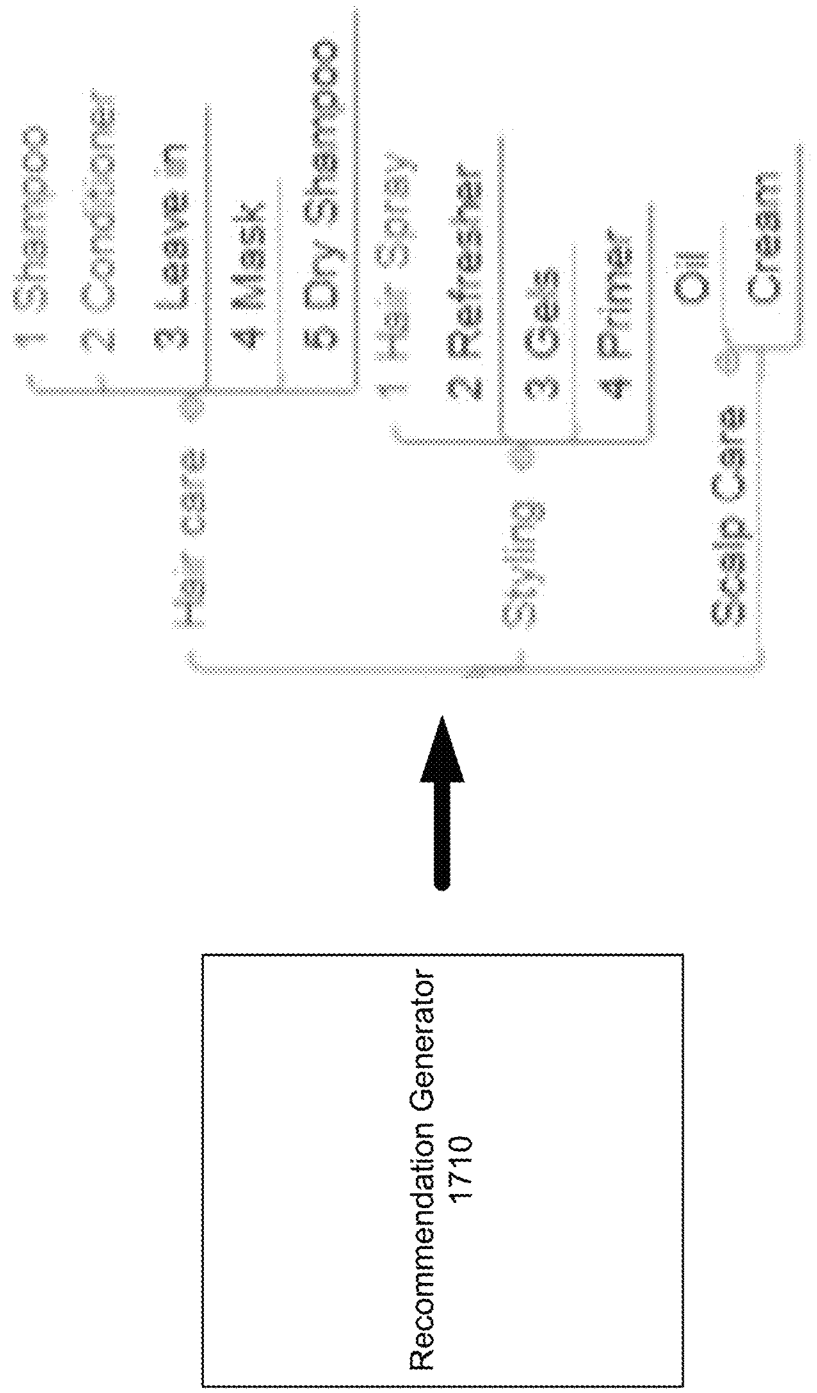
FIG. 21 shows different types of product and treatment recommendations generated by the recommendation generator based on the process described above.

FIG. 21 shows the different types of product and treatment recommendations generated by the recommendation generator based on the process described above. It can be seen that the recommendation can be in the form of a specific product in multiple categories, such as hair care, styling, and scalp care. The hair care products may include shampoo, condition, leave-in condition, mask, and dry shampoo. The styling products may include hair spray, refresher, gels, and primer. The scalp care products may be include oil or cream.

Figure 22:
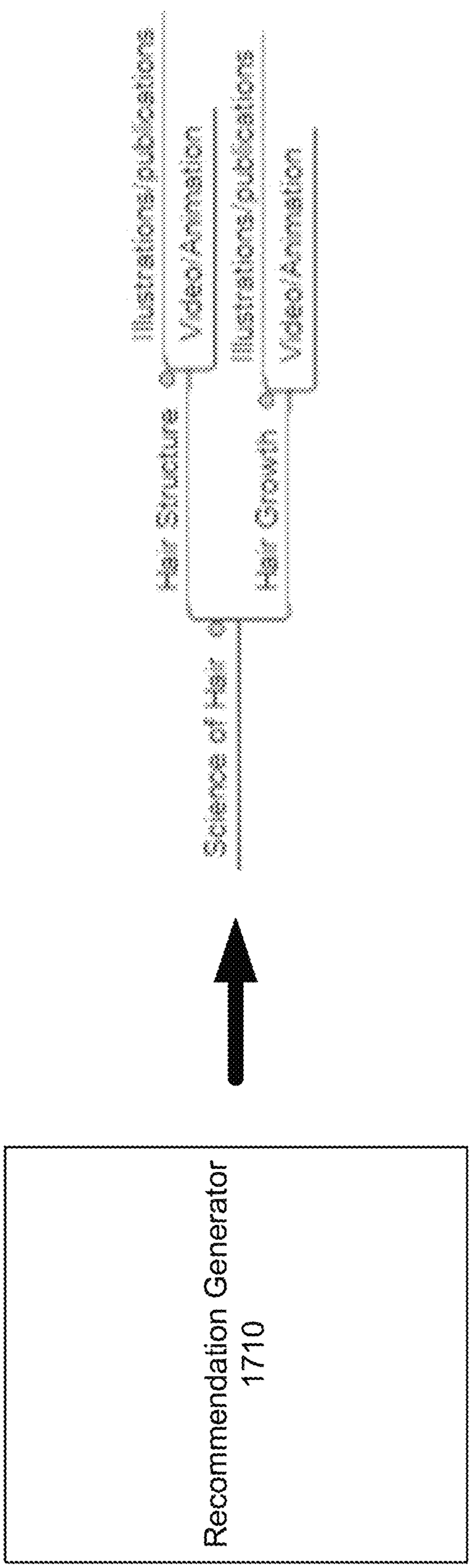
FIG. 22 shows that a recommendation may be in the form of a guide related to the science of hair.

Aside from recommended products, the recommendation generated by the recommendation generator may further include tutorials and guides to help educate the user. As shown in FIG. 22, the recommendation may include guides related to the science of hair, which explains hair structure and hair growth using illustrations, publications, video, and/or animation. Such tutorials can be specific for the user's needs.

Example Scenarios

FIGS. 23-26 show example scenarios of how the application works for different user needs.

Figure 23:
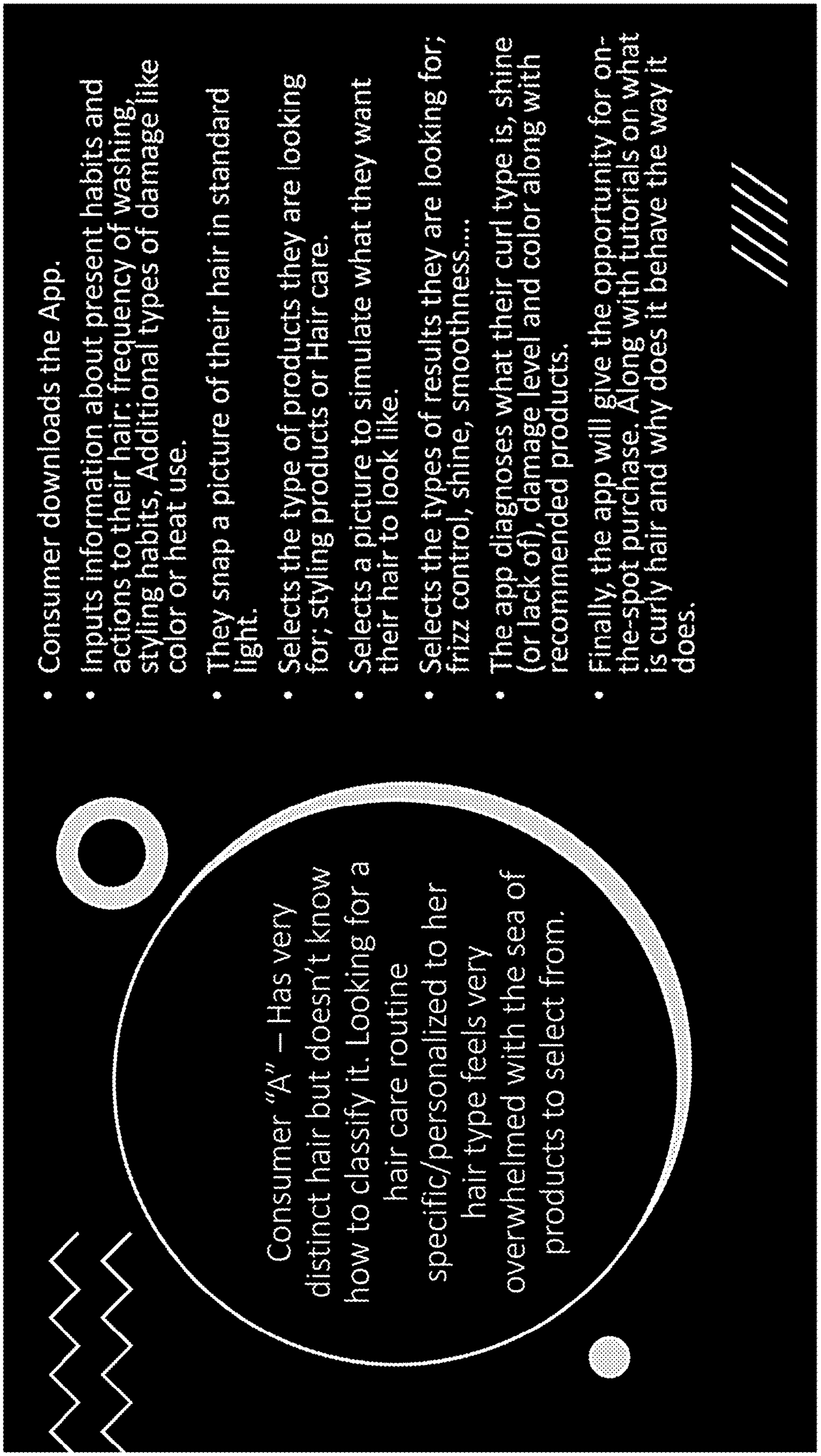
FIG. 23 shows a scenario in which a Consumer "A" has very distinct hair but doesn't know how to classify it.

FIG. 23 illustrate a situation in which a Consumer "A" has very distinct hair but doesn't know how to classify it. In looking for a hair care routine specific/personalized to her hair type, the consumer may feel very overwhelmed with the sea of products to select from. In this scenario, the Consumer A may perform the following using the application according to an embodiment.

- Consumer downloads the App.
- Inputs information about present habits and actions to their hair: frequency of washing, styling habits, Additional types of damage like color or heat use.
- They snap a picture of their hair in standard light.
- Selects the type of products they are looking for; styling products or Hair care.
- Selects a picture to simulate what they want their hair to look like.
- Selects the types of results they are looking for; frizz control, shine, smoothness . . . .
- The app diagnoses what their curl type is, shine (or lack of), damage level and color along with recommended products.
- Finally, the app will give the opportunity for on-the-spot purchase. Along with tutorials on what is curly hair and why does it behave the way it does.

Figure 24:
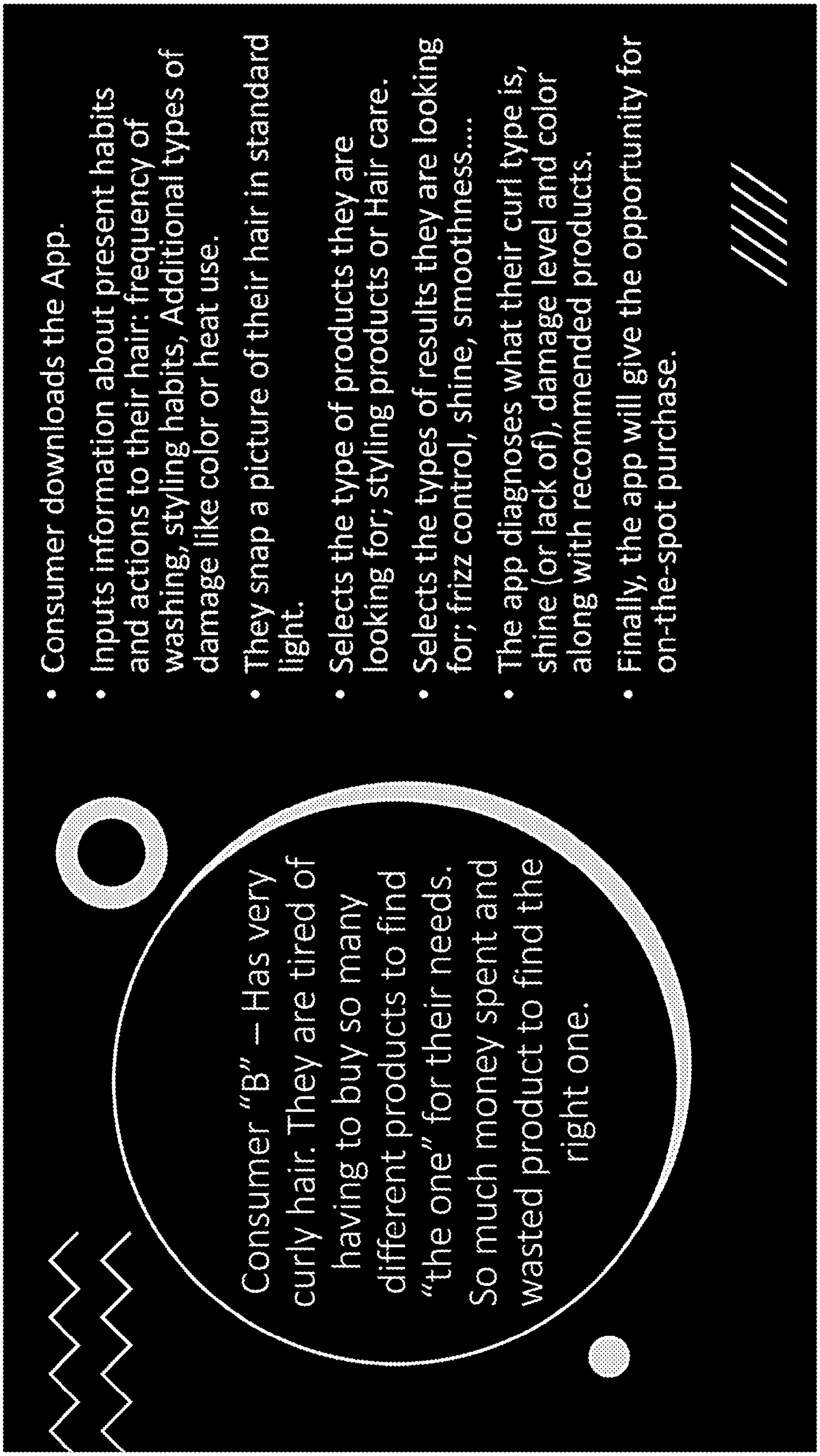
FIG. 24 shows a scenario in which a Consumer "B" has very curly hair and is tired of having to buy so many different products to find "the one" for their needs.

FIG. 24 illustrates a situation in which a Consumer "B" has very curly hair and is tired of having to buy so many different products to find "the one" for their needs. In this scenario, the Consumer B may perform the following using the application according to an embodiment.

- Consumer downloads the App.
- Inputs information about present habits and actions to their hair: frequency of washing, styling habits, Additional types of damage like color or heat use.
- They snap a picture of their hair in standard light.
- Selects the type of products they are looking for; styling products or Hair care.
- Selects the types of results they are looking for; frizz control, shine, smoothness . . . .
- The app diagnoses what their curl type is, shine (or lack of), damage level and color along with recommended products.
- Finally, the app will give the opportunity for on-the-spot purchase.

Figure 25:
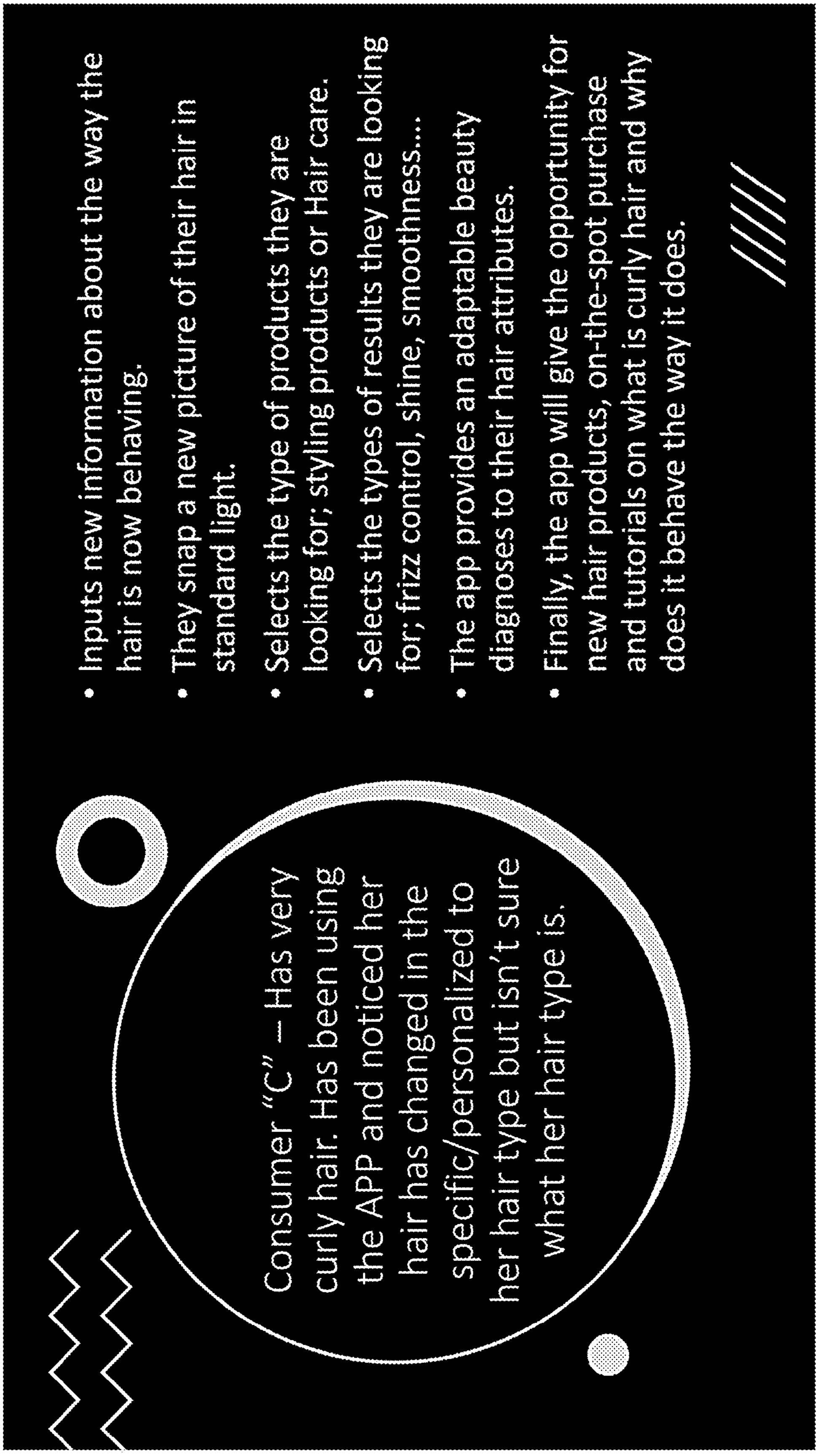
FIG. 25 shows a scenario in which a Consumer "C" has very curly hair and has been using the application and noticed her hair has changed in the specific/personalized to her hair type but isn't sure what her hair type is.

FIG. 25 illustrates a situation in which a Consumer "C" has very curly hair and has been using the application and noticed her hair has changed in the specific/personalized to her hair type but isn't sure what her hair type is. In this scenario, the Consumer C may perform the following using the application according to an embodiment.

- Inputs new information about the way the hair is now behaving.
- They snap a new picture of their hair in standard light.
- Selects the type of products they are looking for; styling products or Hair care.
- Selects the types of results they are looking for; frizz control, shine, smoothness . . . .
- The app provides an adaptable beauty diagnoses to their hair attributes.
- Finally, the app will give the opportunity for new hair products, on-the-spot purchase and tutorials on what is curly hair and why does it behave the way it does.

Figure 26:
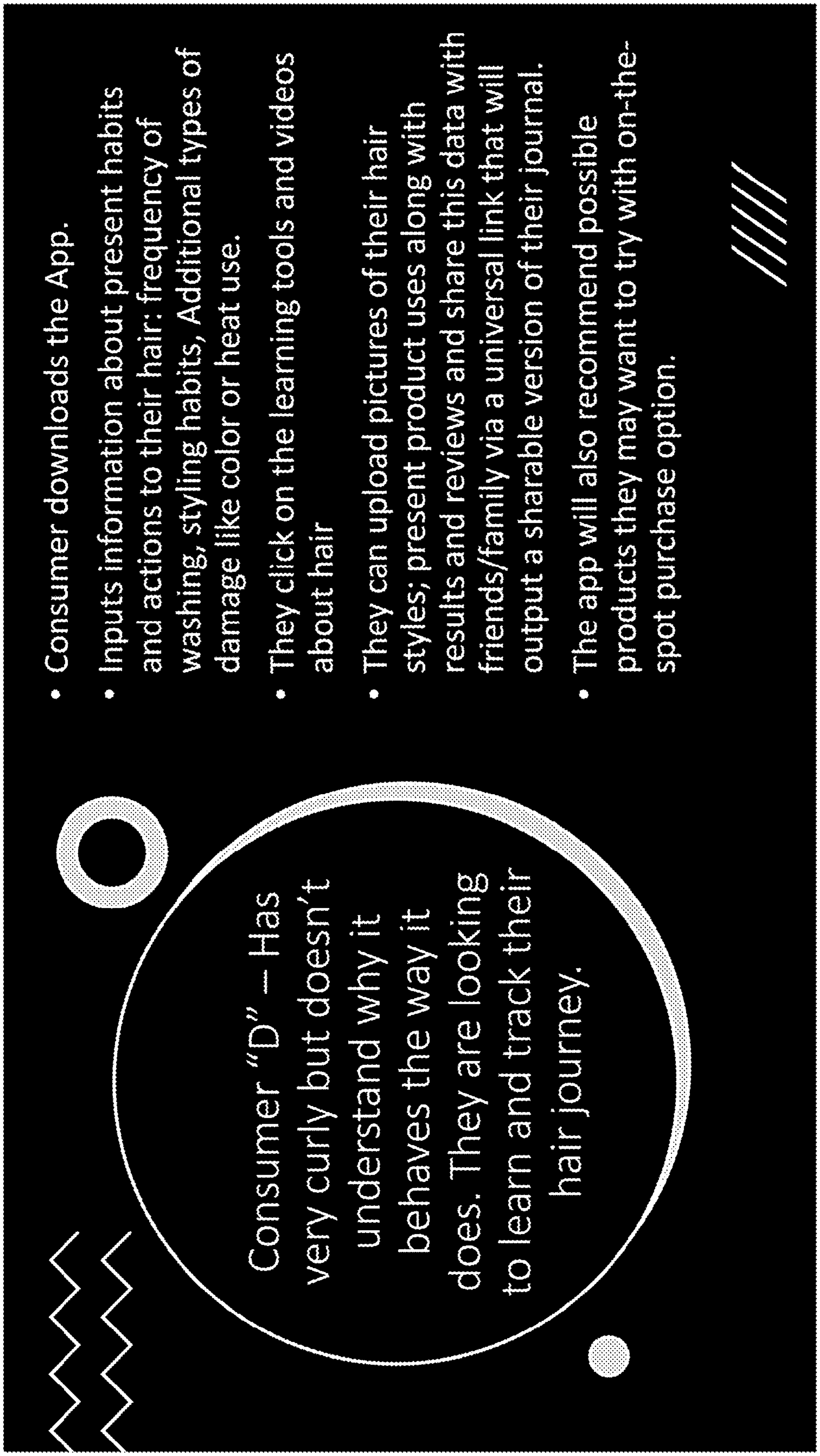
FIG. 26 illustrates a scenario in which Consumer "D" has very curly but doesn't understand why it behaves the way it does.

Finally, FIG. 26 illustrates a situation in which Consumer "D" has very curly but doesn't understand why it behaves the way it does. They are looking to learn and track their hair journey. In this scenario, the Consumer D may perform the following using the application according to an embodiment.

- Consumer downloads the App.
- Inputs information about present habits and actions to their hair: frequency of washing, styling habits, Additional types of damage like color or heat use.
- They click on the learning tools and videos about hair
- They can upload pictures of their hair styles; present product uses along with results and reviews and share this data with friends/family via a universal link that will output a sharable version of their journal.
- The app will also recommend possible products they may want to try with on-the-spot purchase option.

Therefore, the above example scenarios show how the application described in the present embodiments can be meet a variety of consumer needs.

[Enhanced Features]

Training the Product/Treatment Process Recommendation

While the embodiment above illustrates a scenario from an individual user's perspective, an overall system can be realized that utilizes a community of users to enhance both curl diagnosis and product recommendation (similar to some applications we filed for Perso).

Figure 27:
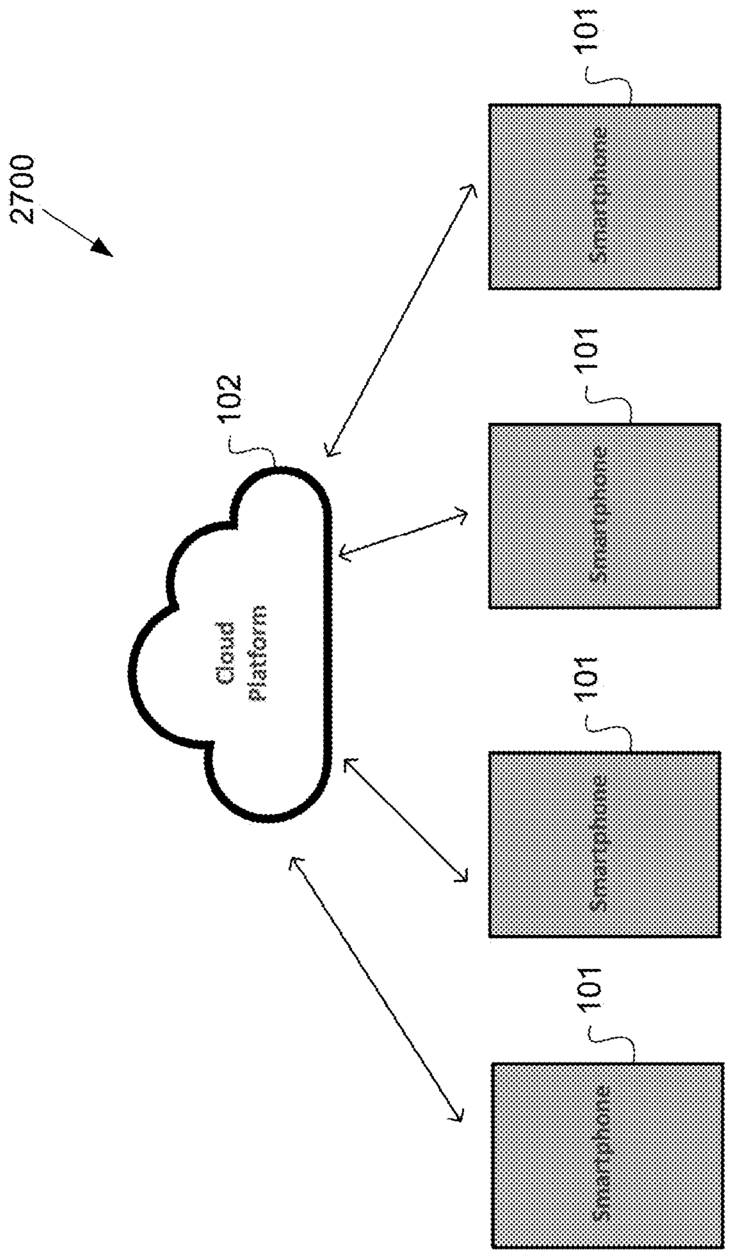
FIG. 27 shows a system in which a plurality of users are connected to the server/cloud platform.

FIG. 27 shows a system 2700 in which a plurality of users are connected to the server/cloud platform 102. As noted above, each user may maintain a "hair journal" to track their results with pictures. While this may be used for adjusting the treatment or recommendation of each individual user, as described above, the "hair journal" can also be used to allow the system to "learn" about how different treatments worked with different users.

In other words, for each user who had successful results using a product or treatment to obtain a desired look, all of the parameters associated with that user may be inputted into a machine learning model. Such parameters may include the following.

User profile

User starting hair condition (curl diagnosis)

User desired look

Percent satisfaction with result

Therefore, with continual inputs, the system will learn the parameters for optimal likelihood of success when a new user having a certain profile, starting hair condition, and desired look starts to use the application.

The use of additional data on the satisfaction can be used to weight a particular treatment, when the visual results between two users is similar, but different treatments were used.

Community Based Training of the Curl Diagnosis

The users provide their own descriptions of what they believe their current hair looks like along with a picture. This can be treated as labeled data within the system itself. Additionally, the users can be asked to identify the type of hair they see in other pictures which may be based on pictures of other users or models. That too provides a labeling process. This also provides a method to better associate the images assigned to curl patterns to the textual words used to describe those images.

In one example, as shown above in FIG. 15, within the application the user may be asked to provide their own input on what curl pattern they believe is present in an image.

There are also may be multiple "gaming" features which are not only useful for entertaining the user, but provide valuable data and feedback to optimize features in the system and provide personalized results for the user.

Figure 28:
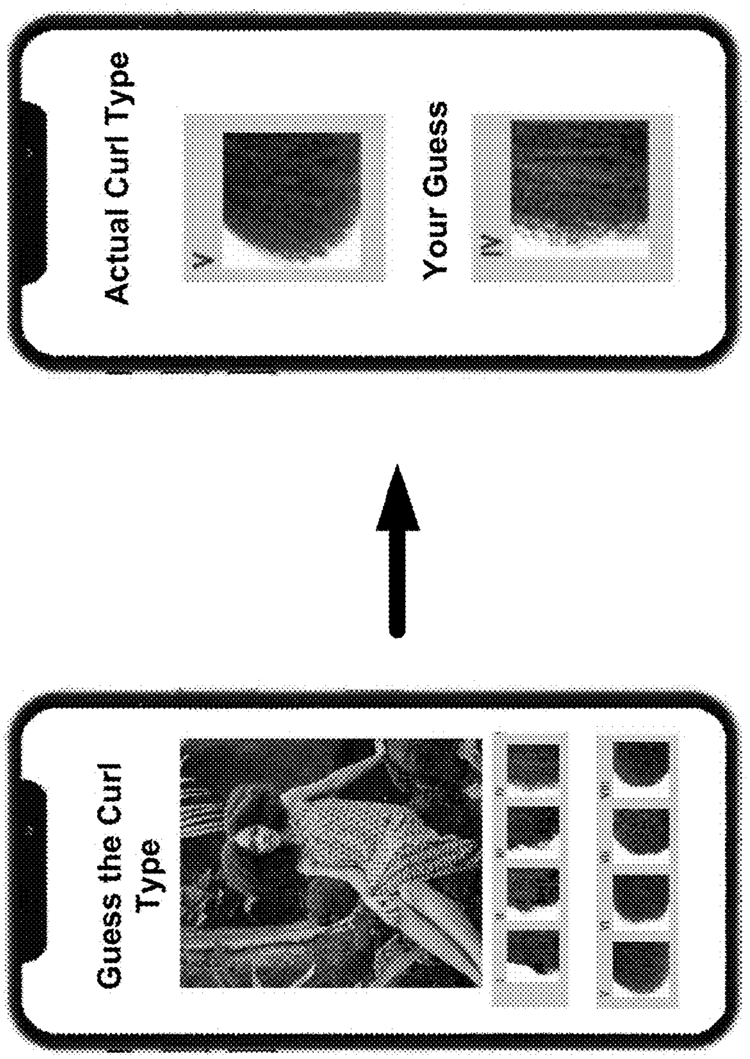
FIG. 28 shows a graphic where data is collected on the user selections on a curl pattern are shown for a displayed image.

For instance, FIG. 28 shows a graphic where data is collected on the user selections on a curl pattern are shown for a displayed image. Additionally, the correct curl pattern is shown in comparison.

The type of game shown in FIG. 28 can be used for at least two purposes. First, it can be used to label an unlabeled image of a curl pattern. In this situation, the "correct answer" shown at the end of the game may be the current highest percentage answer provided by a community of users.

Figure 29:
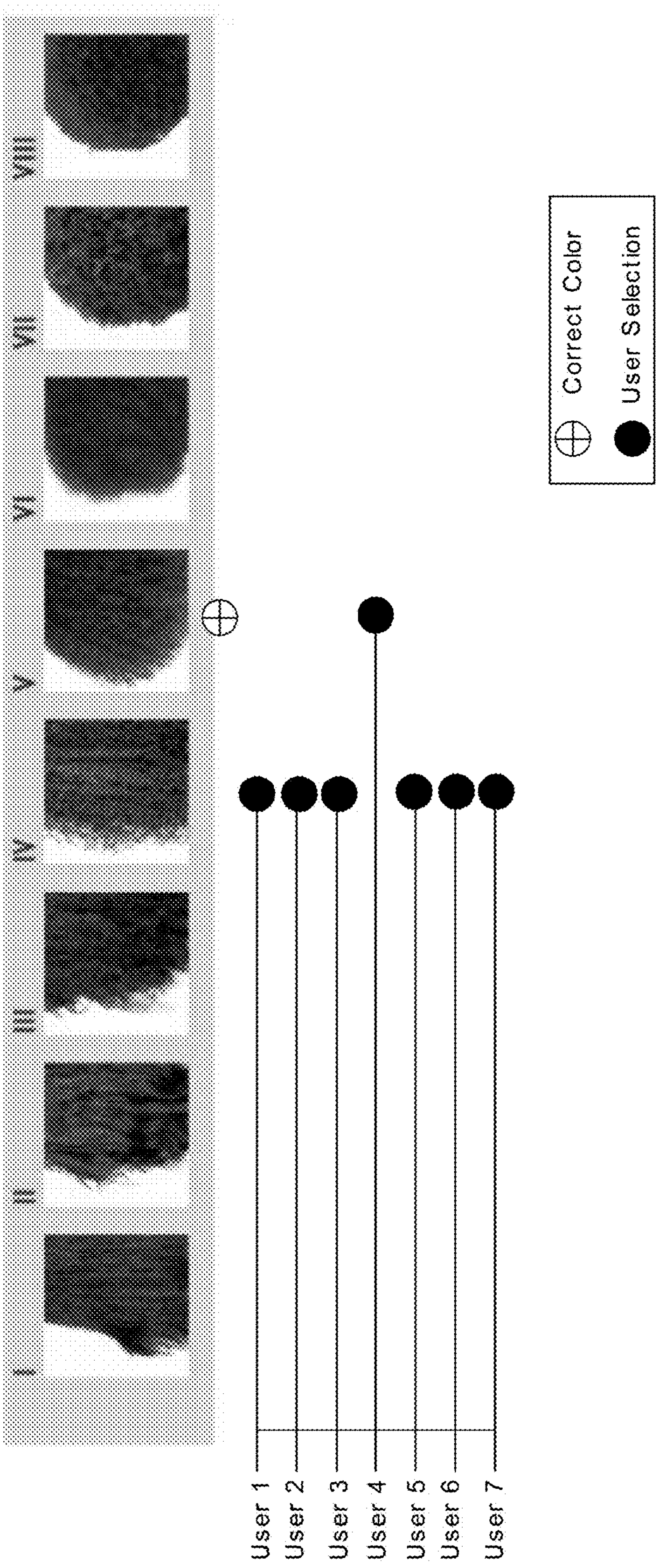
FIG. 29 shows how a cluster of user selections may converge on an incorrect curl pattern label.

Second, it can be used to adjust the entire curl pattern chart itself. In FIG. 29, it can be seen that in the cluster of user selections is not converging on the correct curl pattern label. If a threshold amount of user selections is shifted from a presumed correct curl type on the curl scale, then a correction may be necessary to the types of hair images used for determining a curl type.

As a first advantage of the game shown in FIG. 28, is that the user can develop an eye for curl patterns in hair.

A second advantage of the game shown in FIG. 28 is that each user's selections can be collected by a central server. This data can be very useful. For instance, it can be used to learn preferences of the public at large. For instance, with additional user data, such as the user's age, location, and other lifestyle habits, a cosmetic company can learn if there are trends in user preferences based on different categories and locations of users.

On the Spot Purchasing

While the product recommendation described above can be performed using a large pool of products available from any number of retailers in-store or over the web, it would not be useful to the user if they were in a store when using the app and the recommended product was not available at that location.

Figure 30A:
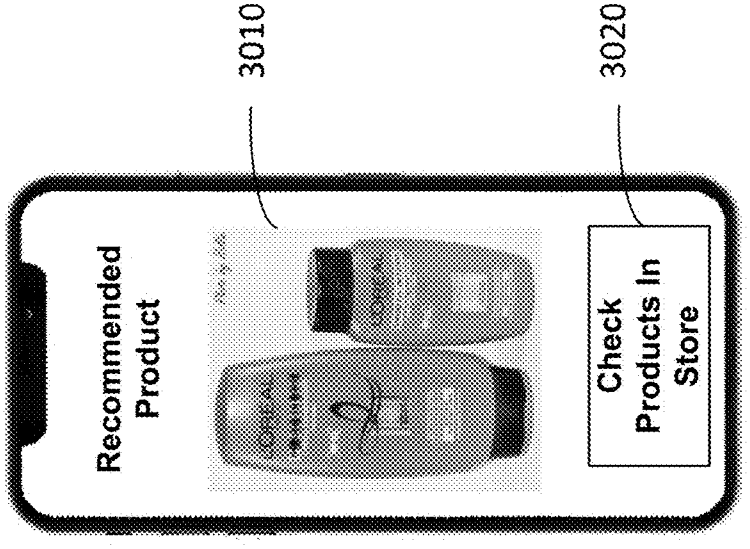
FIG. 30A shows that an overall recommended product may be output by the recommendation generator.
Figure 30A:
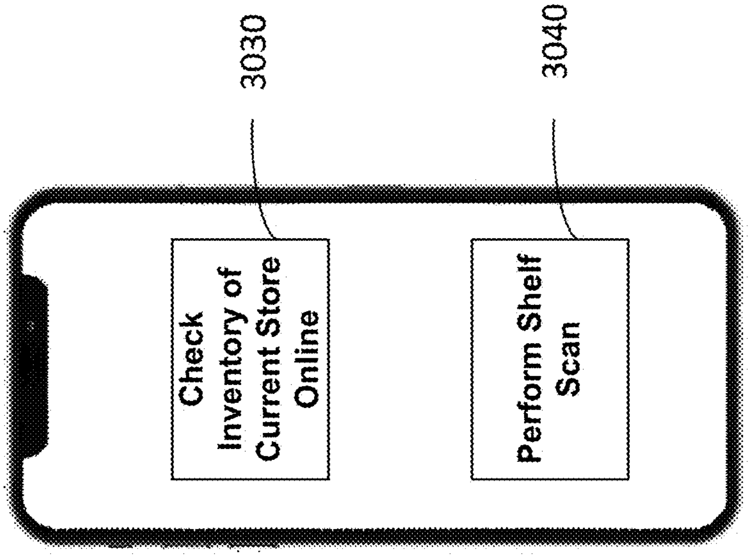

Therefore, the application may include a feature that allows a "store scan" to be performed based on what products are actually on the shelf. First, FIG. 30A shows that an overall recommended product 3010 may be output by the recommendation generator as noted above. However, an additional option 3020 may be displayed to "Check Products In Store."

If the user selects option 3020, then a new screen is displayed at FIG. 30B. The user may then select from two options. A first option 3030 is to check the inventory of the current store online. In this option, using the smartphone GPS function, the application can determine a specific current store that the user is located in, and it can output one or more recommended products currently in inventory at the current store. This option assumes that this information is in fact available online.

Figure 31A:
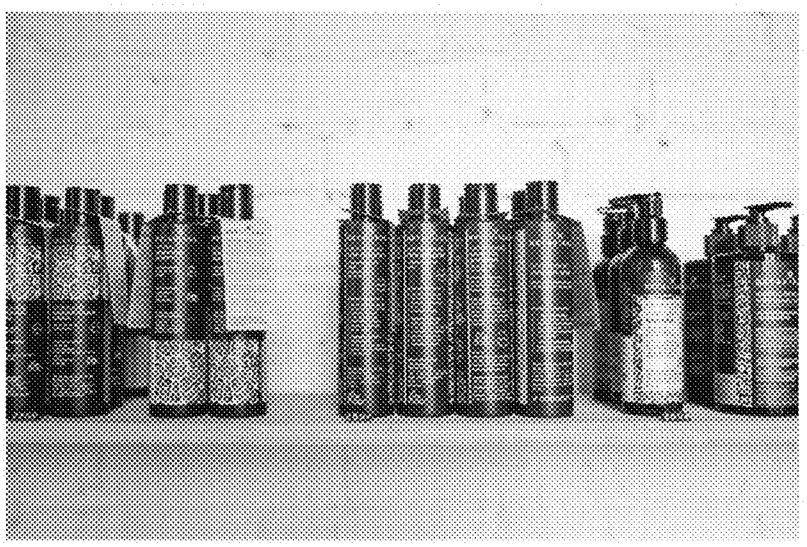
FIG. 31A shows that the user may capture an image of a shelf of hair care products at a retail store.

The second option 3040 is to perform a shelf scan near an actual physical location of the user. If the user chooses this option, then the camera function of the smartphone will be activated and the user may capture an image of a plurality of products located on a shelf. For instance, the user may capture an image of a shelf of hair care products at a retails store as shown in FIG. 31A.

A scan of the products can be performed using methods understood in the art. For instance, a technique may be used as described in U.S. Pat. No. 10,579,962, which is incorporated herein by reference.

Figure 31B:
FIG. 31B shows that as a result of the shelf scan, a suitable product may be visually and/or textually identified.

As a result of the shelf scan, a suitable product may be visually and/or textually identified as shown in FIG. 31B. This product may be similar or have similar ingredients to the recommended product of FIG. 30A.

Obviously, numerous modifications and variations of the present disclosure are possible in light of the above teachings. It is therefore to be understood that within the scope of the appended claims, the invention may be practiced otherwise than as specifically described herein.

What is claimed is:

1. A system, comprising:

at least one server device; and a mobile user device that includes processing circuitry configured to execute an application that receives an input of user information regarding a plurality of characteristics of at least hair of a user including at least a curl pattern of the user; and receives an input of a desired result of treatment of the hair of the user, wherein the processing circuitry of the at least one server device trains a convolutional neural network at least in part on image pairs of originally diagnosed curl patterns and resulting curl patterns labeled with products or treatments that achieved the resulting curl patterns to output product or treatment recommendations based on a combination of image information and textual information;

wherein processing circuitry of the at least one server device receives the input of the user information and the input of the desired result of treatment and outputs a product or treatment recommendation based at least partially on the curl pattern of the user and the desired result of the user, wherein the input of the desired result of treatment comprises a user-selected image of a type of curl pattern, and wherein the processing circuitry of the at least one server device determines the product or treatment recommendation by inputting the input of the user information and the user-selected image of the type of curl pattern into the convolutional neural network that is trained to output the product or treatment recommendations based on the combination of image information and textual information.

2. The system according to claim 1, wherein the input of the desired result comprises textual descriptors of a desired condition of the hair of the user.

3. The system according to claim 1, wherein the outputted product or treatment recommendation is related to at least one of hair care, styling care, and scalp care.

4. The system according to claim 1, wherein the outputted product or treatment recommendation includes illustrations, publications, video, or animation.

5. The system according to claim 1, wherein the processing circuitry of the mobile user device is configured to receive an image of a plurality of hair care products that are at a retail location where the user is located, and the processing circuitry of the at least one server device is configured to generate a recommendation of at least one of the hair care products that are at the retail location.

6. A computer system comprising processing circuitry configured to:

train a convolutional neural network at least in part on image pairs of originally diagnosed curl patterns and resulting curl patterns labeled with products or treatments that achieved the resulting curl patterns to output product or treatment recommendations based on a combination of image information and textual information;

receive input of user information and input of a desired result of treatment of hair of a user and output a product or treatment recommendation based at least partially on a hair curl pattern of the user and the desired result of treatment of the hair of the user, wherein the input of the desired result of treatment comprises a user-selected image of a type of hair curl pattern; and determine the product or treatment recommendation by inputting the input of the user information and the user-selected image of the type of curl pattern into the convolutional neural network that is trained to output the product or treatment recommendations based on the combination of image information and textual information.

7. The computer system according to claim 6, wherein the input of the desired result comprises textual descriptors of a desired condition of the hair of the user.

8. The computer system according to claim 6, wherein the outputted product or treatment recommendation is related to at least one of hair care, styling care, and scalp care.

9. The computer system according to claim 6, wherein the outputted product or treatment recommendation includes illustrations, publications, video, or animation.

10. The computer system according to claim 6, wherein the processing circuitry is further configured to generate a recommendation of at least one hair care product that is available at a retail location where the user is located.

11. A computer-implemented method comprising:

training, by a computer system comprising processing circuitry, a convolutional neural network at least in part on image pairs of originally diagnosed curl patterns and resulting curl patterns labeled with products or treatments that achieved the resulting curl patterns to output product or treatment recommendations based on a combination of image information and textual information;

receiving, by a computer system comprising processing circuitry, input of user information and input of a desired result of treatment of hair of a user; and outputting a product or treatment recommendation based at least partially on a hair curl pattern of the user and the desired result of treatment of the hair of the user, wherein the input of the desired result of treatment comprises a user-selected image of a type of hair curl pattern, and wherein the computer system determines the product or treatment recommendation by inputting the input of the user information and the user-selected image of the type of curl pattern into the convolutional neural network that is trained to output the product or treatment recommendations based on the combination of image information and textual information.

12. The computer-implemented method according to claim 11, wherein the input of the desired result comprises textual descriptors of a desired condition of the hair of the user.

13. The computer-implemented method according to claim 11, wherein the outputted product or treatment recommendation is related to at least one of hair care, styling care, and scalp care.

14. The computer-implemented method according to claim 11, wherein the outputted product or treatment recommendation includes illustrations, publications, video, or animation.

15. The computer-implemented method according to claim 11 further comprising generating a recommendation of at least one hair care product that is available at a retail location where the user is located.

* * * * *